(12) United States Patent
Shapiro

(10) Patent No.: US 6,849,605 B1
(45) Date of Patent: Feb. 1, 2005

(54) INHIBITORS OF SERINE PROTEASE ACTIVITY, METHODS AND COMPOSITIONS FOR TREATMENT OF VIRAL INFECTIONS

(75) Inventor: Leland Shapiro, Denver, CO (US)

(73) Assignee: The Trustees of University Technology Corporation, Boulder, CO (US)

( * ) Notice: Subject to any disclaimer, the term of this patent is extended or adjusted under 35 U.S.C. 154(b) by 0 days.

(21) Appl. No.: 09/518,098

(22) Filed: Mar. 3, 2000

Related U.S. Application Data
(60) Provisional application No. 60/137,795, filed on Jun. 3, 1999, and provisional application No. 60/123,167, filed on Mar. 5, 1999.

(51) Int. Cl.$^7$ ................................................. C07K 5/06

(52) U.S. Cl. ............................ 514/19; 514/18; 530/331

(58) Field of Search ............................... 514/17–19, 2, 514/12; 530/331, 300, 330

(56) References Cited

U.S. PATENT DOCUMENTS 4,818,538 A * 4/1989 Rideout et al. ............. 424/436

FOREIGN PATENT DOCUMENTS

| WO | WO94/07525 | 4/1994 |
| --- | --- | --- |
| WO | WO97/09346 | 3/1997 |
| WO | WO97/09347 | 3/1997 |
| WO | WO97/10222 | 3/1997 |
| WO | WO98/06417 | 2/1998 |
| WO | WO98/49190 | 11/1998 |
| WO | WO99/43308 | 9/1999 |
| WO | WO00/52034 | 9/2000 |

OTHER PUBLICATIONS

Geiben–Lynn Ralf (J Biol Chem 277 (44) 42352–57, 2002).*
Shapiro, Leland (FASEB Journal 15(1), 115–122, 2001).*
Turpin J. A. (Antiviral Research 29 (2–3) 269–77, 1996).*
McNeely (Blood 90, 1141, 1997).*
Vollenweider F (Biochemical Journal 314 ( Pt 2) 521–32, 1996).*
Anderson (J. Biol. Chem. 268, 24887, 1996).*
Adelman S.F. et al., "Protease inhibitors suppress fibrinolytic activity of herpes virus–transformed cells", *J Gen Virol,* 1982, 60(Pt I):15–24.
Altieri, D.C. *J Leukoc Biol 1995, 58,* 120–127.
Aoki H, Akaike T, Abe K, Kuroda M, Arai S, Okamura R, Negi A, Maeda H. *Antiviral effect of oryzacystatin, a proteinase inhibitor in rice, against herpes simplex virus type I in vitro and in vivo.* Antimicrob Agents Chemother Apr. 1995;39(4):846–9.
Beal, M.F., "Mitochondria, Free Radicals, and Neurodegeneration", *Curr. Opin. Neurobiol.,* 1996, 6, 661–666.
Beck, K.F. et al. in *J Exp Biol 1999,* 202, 645–653.

Bjorck L, Grubb A, Kjellen L. Cystatin C, a human proteinase inhibitor, blocks replication of herpes simplex virus. J Virol Feb 1990;64(2):941–3.
Bratt J, Palmblad J. *Cytokine–induced neutrophil1 5 mediated injury of human endothelial cells. J Immunol* Jul. 15, 1997; 159(2):812–8.
Chesnokova NB, Maichuk YF. *Antiproteases in herpetic keratitis.* Metab Pediatr Syst Ophthalmol 1986;9(1):593–6.
Cilberto et al., 1995, *Cell,* 41:531–540.
Deigner, H.P. and R. Kinscherf, "Modulating Apoptosis: Current Applications and Prospects for Future Drug Development", Curr Med *Chem* 1999, 6, 399–414.
Dery, O. and Bunnett, *N. W. Biochem Soc Trans 1999,* 2 7,246–254.
Dery, O. et al. *Am J Physiol 1998,* 2 74, C 1429 –C 1452.
DiIanni CL, Drier DA, Deckman IC, McCann PJ 3d, Liu F, Roizinan B, Colonno RJ, Cordingley MG. Identification of the herpes simplex virus–I protease cleavage sites by direct sequence analysis of autoproteolytic cleavage products. Biol Chem Jan. 25, 1993;268(3):2048–51.
DiIanni CL, Stevens JT, Bolgar M, O'Boyle DR 2nd, Weinheimer SP, Colonno RJ. Identification of the serine residue at the active site of the herpes simplex virus type 1 protease. J Biol Chem Apr. 29, 1994;269(17):12672–6.
Ding, A. et al., in J. *Immunol.* 1990, 145, 940.
Estaquier J, Tanaka M, Suda T, Nagata S, Golstein P, Ameisen JC. Fas–mediated apoptosis of CD4+ and CD8+ T cells from human immunodeficiency virus–infected persons: differential in vitro preventive effect of cytokines and protease antagonists. Blood Jun. 15, 1996;87(12):4959–66.
Flaitz CM, Hicks MJ. "Molecular piracy: the viral link to carcinogenesis." Oral Oncol Nov. 1998;34(6):448–53.
Goureau, O. et al., in *Proc. Natl. Acad. Sci. U.S.A.* 1993, 90, 4276.
Griffin, William C. , "Calculation of HLB Values of Non–Ionic Sufactants", [H. L. B.—The Hydrophilic–Lipoophilic Balance], J. Soc. Cos. Met. Chem., vol. 5, p. 249 (1954).
Heck, D. E. et al., in *J. Biol. Chem.* 1990, 267, 21277.

(List continued on next page.)

*Primary Examiner*—Jon P. Weber
*Assistant Examiner*—David Lukton
(74) *Attorney, Agent, or Firm*—Katten, Muchin, Zavis, Rosenman; Gilberto M. Villacorta; Serge Sira

(57) ABSTRACT

A novel method of treating and preventing viral infection is provided. In particular a method of blocking viral infection facilitated by a serine proteolytic (SP) activity is disclosed, which consists of administering to a subject suffering or about to suffer from viral infection a therapeutically effective amount of a compound having a serine protease inhibitory or serpin activity. Among compounds are $\alpha_1$-antitrypsin (AAT), peptide derivatives from the carboxyterminal end of AAT, and man-made, synthetic compounds mimicking the action of such compounds. The preferred viral infections include retroviral infection such as human immunodeficiency virus (HIV) infection.

4 Claims, 14 Drawing Sheets

OTHER PUBLICATIONS

Holwerda BC. Herpesvirus proteases: targets for novel antiviral drugs. Antiviral Res Jun. 1997;35(1):1–21.
Jabs, Thorsten, "Reactive Oxygen Intermediates as Mediators of Programmed Cell Death in Plants and Animals", *Biochem Pharmacol* 1999 57, 231–245.
Kaufmann, Scott H., Serge Desnoyers, Yvonne Ottaviano, Nancy E. Davidson, and Guy G. Poirier, "Specific Proteolytic Cleavage of Poly(ADP–ribose) Polymerase: An Early Marker of Chemotherapy–induced Apoptosis", *Cancer Res* 1993, 53, 3976.
Kidd, Vincent .J., Proteolytic Activities That Mediate Apoptosis, *Annu Rev Physiol,* 1998, 60, 533.
Kido H, Niwa Y, Beppu Y, Towatari T. *Cellular proteases involved in the pathogenicity of enveloped animal viruses, human immunodeficiency virus, influenza virus A and Sendai virus.* Adv Enzyme Regul 1996;36:325–47.
Kirkeboen, K.A. and Strand, O.A. in *Acta Anaesthesiol Scand 1999, 43,* 275.
Langer, R. *Nature* 1998, 392, 5.
Lomas DA, Elliott PR, Carrell RW. *Commercial plasma alpha1–antitrypsin (Prolastin) contains a confornationally inactive, latent component.* Eur Respir J Mar. 1997;10(3):672–5.
Lowenstein, C. J. and Snyder, S.H. in *Cell* 1992, 70, 705–707.
Lowenstein C. J. et al. *in Proc. Natl. Acad. Sci. USA,* 1993, 90, 9730.
McCall, T.B. et al., in *Biochem. Biophys. Res. Commun.* 1992,186, 680.
Meki AR, Mohey El–Dean ZM. *Serum interleukin–1beta, interleukin–6, nitric oxide and alpha1–antitrypsin in scorpion envenomed children.* Toxicon Dec. 1998;36(12):1851–9.
Molle W. et al. in *J Immunol* 1997, 159, 3555.
Morel, J. B. and Dangle, J.L., *Cell Death Differ* 1997, 4, 67 1; Beal, M. F., *Curr Opin Neurobiol* 1996, 6, 661.

Nathan, C. in *FASEB J.* 1992, 6, 3051.
Ooka T, Hatano Y, Yamamoto M, Ogawa K, Saika S. *Protective effects of human urinary trypsin inhibitor against trypsin–induced relaxation in rat aorta.* Crit Care Med Nov. 1996;24(11):1903–7.
Patel R.P., et al. in *Biochim Biophys Acta* 1999,1411,385–400.
Patel T, Gores GF, Kaufmann SH. *The role of proteases during apoptosis. FASEB J* Apr. 1996;10(5):587–97.
Premack, B. A. and Schall, T. J., "*Chemokine Receptors: Gateways to Inflammation and Infection*", Nature Medicine, 2, 1174–1178 (1996).
Pryor WA, Dooley MM, Church DF. *Mechanisms of cigarette smoke toxicity: the inactivation of human alpha–1–proteinase inhibitor by nitric oxide/isoprene mixtures in air.* Chem Biol Interact Jul. 1985;54(2):171–83.
Punjabi, C. J. et al., in *J. Immunol.* 1992, 149, 2179.
Rehman A, Whiteman M, Halliwell B. *Scavenging of hydroxyl radicals but not of peroxynitrite by inhibitors and substrates of nitric oxide syntheses.* Br J Pharmacol Dec. 1997; 122(8):1702–6.
Schini et al. in *Circ Res* 1994, 74, 24.
Sharpstone D, Rowbottom A, Nelson M, Gazzard B. *Faecal alpha I antitrypsin as a marker of gastrointestinal disease in HIV antibody positive individuals.* Gut Feb. 1996;38(2):206–10.
Shimizu T, Pommier Y. *DNA fragmentation induced by protease activation in p53–null human leukemia HL60 cells undergoing apoptosis following treatment with the topoisomerase I inhibitor camptothecin: cell–free system studies.* Exp Cell Res Aug. 1, 1996;226(2):292–301.
Smith, M. E. in *Neurochem Res* 1999, 24, 261.
Wood, E.R. et al. in *Biochem Biophys Res Commun* 1993, 191, 767–74.

* cited by examiner

SEQUENCE LISTING

<160> NUMBER OF SEQ ID NOS: 19

<210> SEQ ID NO 1
<211> LENGTH: 5
<212> TYPE: PRT
<213> ORGANISM: Homo sapiens

<400> SEQUENCE: 1

Phe Val Phe Leu Met
 1               5

<210> SEQ ID NO 2
<211> LENGTH: 5
<212> TYPE: PRT
<213> ORGANISM: Homo sapiens

<400> SEQUENCE: 2

Phe Val Phe Ala Met
 1               5

<210> SEQ ID NO 3
<211> LENGTH: 5
<212> TYPE: PRT
<213> ORGANISM: Homo sapiens

<400> SEQUENCE: 3

Phe Val Ala Leu Met
 1               5

<210> SEQ ID NO 4
<211> LENGTH: 5
<212> TYPE: PRT
<213> ORGANISM: Homo sapiens

<400> SEQUENCE: 4

Phe Leu Phe Leu Ile
 1               5

<210> SEQ ID NO 5
<211> LENGTH: 5
<212> TYPE: PRT
<213> ORGANISM: Homo sapiens

<400> SEQUENCE: 5

Phe Val Phe Leu Ala
 1               5

<210> SEQ ID NO 6
<211> LENGTH: 5
<212> TYPE: PRT
<213> ORGANISM: Homo sapiens

<400> SEQUENCE: 6

Phe Leu Val Phe Ile
 1               5

<210> SEQ ID NO 7
<211> LENGTH: 5
<212> TYPE: PRT
<213> ORGANISM: Homo sapiens

<400> SEQUENCE: 7

Phe Leu Met Ile Ile
 1               5

<210> SEQ ID NO 8
<211> LENGTH: 5
<212> TYPE: PRT
<213> ORGANISM: Homo sapiens

<400> SEQUENCE: 8

Phe Leu Phe Val Leu
 1               5

```
<210> SEQ ID NO 9
<211> LENGTH: 5
<212> TYPE: PRT
<213> ORGANISM: Homo sapiens

<400> SEQUENCE: 9

Phe Leu Phe Val Val
 1               5

<210> SEQ ID NO 10
<211> LENGTH: 5
<212> TYPE: PRT
<213> ORGANISM: Homo sapiens

<400> SEQUENCE: 10

Phe Leu Phe Phe Ile
 1               5

<210> SEQ ID NO 11
<211> LENGTH: 5
<212> TYPE: PRT
<213> ORGANISM: Homo sapiens

<400> SEQUENCE: 11

Phe Leu Met Phe Ile
 1               5

<210> SEQ ID NO 12
<211> LENGTH: 5
<212> TYPE: PRT
<213> ORGANISM: Homo sapiens

<400> SEQUENCE: 12

Phe Met Leu Leu Ile
 1               5

<210> SEQ ID NO 13
<211> LENGTH: 5
<212> TYPE: PRT
<213> ORGANISM: Homo sapiens

<400> SEQUENCE: 13

Phe Ile Ile Met Ile
 1               5

<210> SEQ ID NO 14
<211> LENGTH: 5
<212> TYPE: PRT
<213> ORGANISM: Homo sapiens

<400> SEQUENCE: 14

Phe Leu Phe Cys Ile
 1               5

<210> SEQ ID NO 15
<211> LENGTH: 5
<212> TYPE: PRT
<213> ORGANISM: Homo sapiens

<400> SEQUENCE: 15

Phe Leu Phe Ala Val
 1               5

<210> SEQ ID NO 16
<211> LENGTH: 5
```

```
<212> TYPE: PRT
<213> ORGANISM: Homo sapiens

<400> SEQUENCE: 16

Phe Val Tyr Leu Ile
 1               5

<210> SEQ ID NO 17
<211> LENGTH: 5
<212> TYPE: PRT
<213> ORGANISM: Homo sapiens

<400> SEQUENCE: 17

Phe Ala Phe Leu Met
 1               5

<210> SEQ ID NO 18
<211> LENGTH: 5
<212> TYPE: PRT
<213> ORGANISM: Homo sapiens

<400> SEQUENCE: 18

Ala Val Phe Leu Met
 1               5

<210> SEQ ID NO 19
<211> LENGTH: 414
<212> TYPE: PRT
<213> ORGANISM: Homo sapiens

<400> SEQUENCE: 19

Met Pro Ser Ser Val Ser Trp Gly Ile Leu Leu Leu Ala Gly Leu Cys
 1               5                  10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala Ser Thr Asn Ile Phe Phe Ser Pro Val Ser Ile Ala Thr Ala
 65                  70                  75                  80

Phe Ala Met Leu Ser Leu Gly Thr Lys Ala Asp Thr His Asp Glu Ile
                85                  90                  95

Leu Glu Gly Leu Asn Phe Asn Leu Thr Glu Ile Pro Glu Ala Gln Ile
            100                 105                 110

His Glu Gly Phe Gln Glu Leu Leu Arg Thr Leu Asn Gln Pro Asp Ser
        115                 120                 125

Gln Leu Gln Leu Thr Thr Gly Asn Gly Leu Phe Leu Ser Glu Gly Leu
    130                 135                 140

Lys Leu Val Asp Lys Phe Leu Glu Asp Val Lys Lys Leu Tyr His Ser
145                 150                 155                 160

Glu Ala Phe Thr Val Asn Phe Gly Asp Thr Glu Glu Ala Lys Lys Gln
                165                 170                 175

Ile Asn Asp Tyr Val Glu Lys Gly Thr Gln Gly Lys Ile Val Asp Leu
            180                 185                 190

Val Lys Glu Leu Asp Arg Asp Thr Val Phe Ala Leu Val Asn Tyr Ile
        195                 200                 205

Phe Phe Lys Gly Lys Trp Glu Arg Pro Phe Glu Val Lys Asp Thr Glu
    210                 215                 220
```

```
Glu Glu Asp Phe His Val Asp Gln Val Thr Thr Val Lys Val Pro Met
225                 230                 235                 240

Met Lys Arg Leu Gly Met Phe Asn Ile Gln His Cys Lys Lys Leu Ser
                245                 250                 255

Ser Trp Val Leu Leu Met Lys Tyr Leu Gly Asn Ala Thr Ala Ile Phe
                260                 265                 270

Phe Leu Pro Asp Glu Gly Lys Leu Gln His Leu Glu Asn Glu Leu Thr
            275                 280                 285

His Asp Ile Ile Thr Lys Phe Leu Glu Asn Glu Asp Arg Arg Ser Ala
            290                 295                 300

Ser Leu His Leu Pro Lys Leu Ser Ile Thr Gly Thr Tyr Asp Leu Lys
305                 310                 315                 320

Ser Val Leu Gly Gln Leu Gly Ile Thr Lys Val Phe Ser Asn Gly Ala
                325                 330                 335

Asp Leu Ser Gly Val Thr Glu Glu Ala Pro Leu Lys Leu Ser Lys Ala
                340                 345                 350

Val His Lys Ala Val Leu Thr Ile Asp Glu Lys Gly Thr Glu Ala Ala
            355                 360                 365

Gly Ala Met Phe Leu Glu Ala Ile Pro Met Ser Ile Pro Pro Glu Val
    370                 375                 380

Lys Phe Asn Lys Pro Phe Val Phe Leu Met Ile Glu Gln Asn Thr Lys
385                 390                 395                 400

Ser Pro Leu Phe Met Gly Lys Val Val Asn Pro Thr Gln Lys
                405                 410
```

INHIBITORS OF SERINE PROTEASE ACTIVITY, METHODS AND COMPOSITIONS FOR TREATMENT OF VIRAL INFECTIONS

This application claims priority to U.S. Provisional Application No. 60/123,167 filed Mar. 5, 1999 and U.S. Provisional Application No. 60/137,795 filed Jun. 3, 1999 both of which are hereby incorporated by reference.

FIELD OF THE INVENTION

In general, the present invention relates to enzyme inhibitors and their respective ligands. More particularly, the present invention relates to substances exhibiting inhibitory activity toward retroviral replication and spread, which are facilitated or mediated by serine protease activity.

BACKGROUND AND SUMMARY OF THE INVENTION

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine (Asp-His-Ser) at the active site.

The naturally occurring serine protease inhibitors are usually, but not always, polypeptides and proteins which have been classified into families primarily on the basis of the disulfide bonding pattern and the sequence homology of the reactive site. Serine protease inhibitors (serpins) have been found in microbes, in the tissues and fluids of plants, animals, insects and other organisms. Protease inhibitor activities were first discovered in human plasma by Ferni and Pernossi in 1894. At least nine separate, well-characterized proteins are now identified, which share the ability to inhibit the activity of various proteases. Several of the inhibitors have been grouped together, namely alpha-1-proteinase inhibitor, antithrombin III, antichymotrypsin, C1 inhibitor, eglin, and alpha-2-antiplasmin, which are directed against various serine proteases, i.e., leukocyte elastase, thrombin, cathepsin G, chymotrypsin, plasminogen activators, and plasmin. These are referred to as the alpha-1-proteinase inhibitor class. The protein alpha-2-macroglobulin inhibits members of all four catalytic classes: serine, cysteine, aspartic, and metalloproteases. However, other types of protease inhibitors are class specific. The alpha-1-proteinase inhibitor (also known as $\alpha_1$-antitrypsin or AAT) and inter-alpha-trypsin inhibitor inhibit only serine proteases, alpha-1-cysteine protease inhibitor inhibits cysteine proteases, and alpha-1-anticollagenase inhibits collagenolytic enzymes of the metalloenzyme class.

AAT is a glycoprotein of MW 51,000 with 394 amino acids and 3 oligosaccharide side chains. Human AAT was named anti-trypsin because of its initially discovered ability to inactivate pancreatic trypsin. Human AAT is a single polypeptide chain with no internal disulfide bonds and only a single cysteine residue normally intermolecularly disulfide-linked to either cysteine or glutathione. The reactive site at position 358 of AAT contains a methionine residue, which is labile to oxidation upon exposure to tobacco smoke or other oxidizing pollutants. Such oxidation may reduce the biological activity of AAT; therefore substitution of another amino acid at that position, i.e. alanine, valine, glycine, phenylalanine, arginine or lysine, produces a form of AAT which is more stable. AAT can be represented by the following formula: MPSSVSWGILLAGLC CLVPVSLAEDPQGDAAQKTDTSHHDQDHPTFNKIT PNLAEFAFSLYRQLASTNEFFSPVSIATAFAMLSLGT KADTHDEILEGLNFNLTEIPEAQDHPTFQELLRTL NQPDSQLQLTTGNGLFLSEGLKLVDKFLEDVKKLY HSEAFKKVNFGDTEEAKKQINDYVEKGTQGKI VDLVKELDRDTVFALVNYWFKGKWERPFEVKDTE EEDFHVDQVTTVKVPMMKRLGMFNIQHCKKLSS WVLLMKYLGNATAIFFLPDEGKLQHLENELTHDU TKFLENEDRRSASLHLPKLSITGTYDLKSVLGQIG ITKVFSNGADLSGVTEEAPLKMSKAVHKAVLTID EKGTEAAGAMAFLEAIPMSIPPEVKFNKPQNTKS PLFMGKVNPQK (SEQUENCE ID. NO. 19).

(Details of the sequence can be found for example in U.S. Pat. No. 5,470,970, incorporated herein by reference in its entirety).

The C-tenrnini of human antitrypsin (AAT), is homologous to antithrombin (ATIII), antichymotrypsin (ACT), C1-inhibitor, tPA-inhibitor, mouse AT, mouse contrapsin, barley protein Z, and ovalbumin. Its normal plasma concentration ranges from 1.3 to 3.5 mg/ml although it can behave as an acute phase reactant by increasing 3-4-fold during host response to inflammation and/or tissue injury such as with pregnancy, acute infection, and tumors. Alpha-1-antitrypsin, known to be an acute phase protein in humans, is augmented in autoimmune diseases such as systemic lupus erythematosus (SLE), rheumatoid arthritis (RA), mixed connective tissue disease (MCTD), Sjogren syndrome, scleroderma, and other sclerotic diseases. AAT may play an important role as an early marker for the diagnosis of such autoimmune disorders.

AAT easily diffuses into tissue spaces and forms a 1:1 complex with a target protease, principally neutrophil elastase. Human neutrophil elastase (NE) is a proteolytic enzyme secreted by polymorphonuclear leukocytes in response to a variety of inflammatory stimuli. The degradative capacity of NE, under normal circumstances, is modulated by relatively high plasma concentrations of $\alpha_1$-antitrypsin (AAT). However, stimulated neutrophils produce a burst of active oxygen metabolites, some of which (hypochlorous acid for example) are capable of oxidizing a critical methionine residue in AAT. Oxidized AAT has been shown to have a limited potency as a NE inhibitor and it has been proposed that alteration of this protease/antiprotease balance permit NE to perform its degradative functions in a non-localized and uncontrolled fashion.

Other enzymes such as trypsin, chymotrypsin, cathepsin G, plasmin, thrombin, tissue kallikrein, and factor Xa can also serve as substrates. The enzyme/inhibitor complex is removed from circulation by binding to serpin-enzyme complex (SEC) receptor and catabolized by the liver and spleen cells. Humans with circulating levels of AAT less than 15% of normal are susceptible to the development of lung disease, e.g., familial emphysema, at an early age. Therefore, it appears that this inhibitor represents an important part of the defense mechanism against attack by serine proteases.

In some instances the degradative action of serine proteases results in serious pathological conditions or disease states. For example, elastase is a protease which causes degradation and fragmentation of elastic fibers as a result of its proteolytic activity on rubber-like elastin. Other connective tissue proteins, such as type I, III, and IV collagens, the protein portion of proteoglycans, and laminin may be also cleaved by elastase. Tissues comprising the lungs, bronchi, ear, and skin contain large amounts of elastin. Excessive degradation of elastin has also been associated with arthritis, atherosclerosis, certain skin diseases, pulmonary emphysema and acute respiratory-distress syndrome. Therefore, by inhibiting the activity of elastase it is possible to treat a wide variety of pathological conditions including pulmonary emphysema, various clotting disorders and inflammatory processes.

One illustration of the importance of the catalytic activity of serine proteases is provided by the role of human neutrophil elastase and one of its natural inhibitors, AAT, in the pathogenesis of emphysema or cystic fibrosis. In the lungs of healthy individuals there is a balance between the levels of elastase and its inhibitors. The elastase serves in the repair and turnover of connective tissues (elastin) and the AAT is involved in the regulation and clearance of elastase. Disruption of the elastase/AAT balance leads to increased elastin degradation and, hence, to elastic tissue destruction. A prolonged imbalance leads to an irreversible dilation of pulmonary airways and damage to the respiratory tissues of the lung, a condition known as pulmonary emphysema. As another example, oxidants from the condensate of cigarette smoke have been shown to drastically reduce the elastase binding affinity of AAT by oxidizing a methionine residue within the reactive site. A final example involves both elevated levels of elastase and simultaneously lower levels of functional AAT inhibitor. The inflammatory response to foreign particulate matter or cigarette smoke leads to elevated levels of polymorphonuclear leukocytes in the lungs. These cells disrupt the protease/protease inhibitor balance by secretion of proteolytic enzymes, e.g., elastase. They also secrete oxidants including myeloperoxidase which appear to oxidatively inactive AAT.

So far, AAT is one of few naturally-occurring mammalian serine protease inhibitors clinically approved for the therapy of protease imbalance. Therapeutic AAT became commercially available in the mid 80's and is prepared by various purification methods (see for example Bollen et al., U.S. Pat. Nos. 4,629,567; Thompson et al., 4,760,130; U.S. Pat. No. 5,616,693; WO 98156821). PROLASTIN® is a trademark for a purified variant of AAT, is currently sold by Bayer Company (U.S. Pat. No. 5,610,285 Lebing et al., Mar. 11, 1997). Recombinant unmodified and mutant variants of AAT produced by genetic engineering methods from transformed cells are also known (U.S. Pat. No. 4,711,848); methods of delivery are also known, e.g., AAT gene therapy/delivery (U.S. Pat. No. 5,399,346 to French Anderson et al.).

Human Immunodeficiency Virus (HIV)

The replication of HIV requires protease activity required for the cleavage of gag-pol precursor proteins. This enzymatic activity is similar to activity of renin—aspartyl protease produced by the kidney. The close relationship between renin and HIV encoded protease led to an accelerated generation of specific HIV-1 protease inhibitors as effective agents in treatment of AIDS (Scharpe, et al., "Proteases and their inhibitors: today and tomorrow", Biochimie, 73(1):121–6 (1991). Many therapeutic agents directed against HIV protease have been developed as a consequence and used successfully in AIDS patients. For example, indinavir and crixivan are aspartyl protease inhibitors, which inhibit cleavage of pre-protein of HIV by viral own protease and thereby suppress viral proliferation. Lezdey et al., (U.S. Pat. No. 5,532,215) disclose the method of using AAT, Secretory Leukocyte Protease Inhibitor (SLPI), and alpha antichymotrypsin (AAC) for inhibition of proliferation of a variety of viruses that require gag-pol cleavage. They claim that AAT, SLPI, and AAC, generally known as serine protease inhibitors, inhibit such viruses by binding to viral or cellular aspartic protease. While it is unknown whether this mechanism may take place in such circumstances, several lines of evidence exist, which indicate that serine protease inhibitors may interfere with viral replication through inhibition of host's serine proteases but not HIV encoded aspartyl protease.

Several serine proteases of the human host have been identified in the past as being involved in HIV infection. Investigators argued that the endoproteolytic cleavage of the envelope glycoprotein precursor (gp160) of the HIV by a cellular protease is required for full activation of the virus. The first one, so-called Kunitz-type basic proteinase or tryptase TL2, was proposed by Kido et al., "*A novel membrane-bound serine esterase in human T4+lymphocytes immunologically reactive with antibody inhibiting syncytia induced by HIV-1. Purification and characterization*", J. Biol. Chem., 15;265(35):21979–85 (1990); and Brinkmann et al., "*Inhibition of tryptase TL2from human T4+lymphocytes and inhibition of HIV-1 replication in HIV-1 cells by recombinant aprotinin and bikunin homologues*", J Protein Chem, 16(6):651–60), (1997). Accordingly, the recombinant (K15R M52E) aprotinin—a Kunitz-type inhibitor—reduced HIV-1 replication in H9 cells at a concentration of 50 microM. (Auerswald et al., "*K15R M52E*) *aprotinin is a weak Kunitz-type inhibitor of HIV-1 replication in H9 cells*" Biomed Biochim Acta, 50(4–6):697–700 (1991)).

A calcium-independent processing protease, viral envelope glycoprotein maturase (VEM), converted HIV envelope glycoprotein precursor gp160 to gp120 and gp41 and was identified by Kamoshita et al., (Kamoshita et al., "*Calcium requirement and inhibitor spectrum for intracellular HIV type 1 gp160 processing in cultured HeLa cells and CD4+lymphocytes: similarity to those of viral envelope glycoprotein maturase*", J Biochem, Jun. 117(6):124453) (Tokyo 1995).

A neutralizing epitope of HIV on external envelope glycoprotein (gp120) was found to have homologous sequences to inter-alpha-trypsin inhibitor(ITI). Human urinary trypsin inhibitor(UTI), a protein indistinguishable from M, as well as synthetic peptides including epitope beta inhibited in syncytium formation caused by the HIV-1-infected CCRF-CEM and uninfected Molt-4 cells in a dose-dependent manner (0.1–1 mM). These findings suggested that epitope on gp120 could be a substrate for trypsin-like protease upon HIV-1 infection (Koito et al., "*A neutralizing epitope of human immunodeficiency virus type 1 has homologous amino acid sequences with the active site of inter-alpha-trypsin inhibitor*", Int Immunol, 1(6):613–8) (1989).

A naturally occurring serine protease inhibitor or serpin, secretory leukocyte protease inhibitor (SLPI) was shown to inhibit HIV in monocytic cells. SLPI did not appear to act on the a virus directly, but rather through interaction with the host cell (McNeely et al., "*Secretory leukocyte protease inhibitor: a human saliva protein exhibiting anti-human immunodeficiency virus 1 activity in vitro*", J Clin Invest, 96(1):45664) (1995).

Hallenberger et al., identified the serine protease furin, which recognizes the amino-acid sequence Arg-X-Lys/Arg-Arg as a cleavage site, as involved in HIV infection (Hallenberger et al., "*Inhibition of furin-mediated cleavage activation of HIV-1 glycoprotein gp160*", Nature, 26;360 (6402):358–61) (1992). In addition to furin, other subtilisin/kexin-like convertases including PACE4, PC5/6-B and PC1 were also proposed as candidate enzymes and the co-expression of the [Arg355, Arg358]-alpha-1-antitrypsin—furin-directed Portland variant—was shown to potently inhibit the processing of both gp160 and gp120 by these convertases (Vollenweider, et al., "*Comparative cellular processing of the human immunodeficiency virus (HIV-1) envelope glycoprotein gp160 by the mammalian subtilisin/kexin-like convertases*", Biochem, 1;314 (Pt2) :521–32) (1996). Another mutant variant of AAT, directed against furin, was recently proposed as a specific HIV inhibitor (Anderson et al., "*Inhibition of HIV-1 gp160-dependent membrane fusion by a furin-directed alpha 1-antitrypsin variant*", J Biol Chem, 268(33):24887–91 (1993); and also U.S. Pat. No. 5,604,201, incorporated herein by reference in its entirety).

Meanwhile, Decroly et al., believe that kexin/subtilisin-related endoproteases including furin, PC5/6, and the newly cloned PC7 (LPC/PC7) are main convertase enzyme candidates responsible for the cleavage of the HIV envelope glycoprotein (Decroly, et al., "*Identification of the paired basic convertases implicated in HIV gp160 processing based on in vitro assays and expression in CD4(+) cell lines*", J Biol Chem, 271(48):30442–50) (1996).

A human analogue of endoprotease Kex2p, from the yeast *Saccharomyces cerevisiae*, was proposed as a cellular enzyme processing HIV envelope glycoprotein precursor (Moulard, et al., "*Kex2p: a model for cellular endoprotease processing human immunodeficiency virus type 1 envelope glycoprotein precursor*", Eur J Biochem, 225(2):565–72 (1994); Franzusoff, et al., "*Biochemical and genetic definition of the cellular protease required for HIV-1 gp16 processing*", J Biol Chem, 270(7):3154–9) (1994). These serine proteases when expressed within the host cell were postulated to operate not only on the cell surface but also intracellularly.

A cathepsin G-like proteinase at the surface of U-937 cells reacting with the V3 loop of HIV-1 gp120 was reported by Avril et al., (Avril, et al., "*Identification of the U-937 membrane-associated proteinase interacting with the V3 loop of HIV-1 gp120 as cathepsin G*", FEBS Lett, 345(1) :81–6) (1994).

At least five separate T lymphocyte-derived enzymes, mostly zinc-dependent metalloproteinases with affinity to HIV envelope, were identified by Harvima et al., (Harvima et al., "*Separation and partial characterization of proteinases with substrate specificity for basic amino acids from human MOLT-4 T lymphocytes: identification of those inhibited by variable-loop-V3 peptides of HIV-1 (human immunodeficiency virus-1) envelope glycoprotein*", Biochem J, 292 (Pt 3):711–8) (1993).

Acrosin, a serine protease from semen, was also identified as being involved in HIV infection (Bourinbaiar, et al., "*Acrosin inhibitor, 4'-acetamidophenyl 4-guanidinobenzoate, an experimental vaginal contraceptive with anti-HIV activity*", Contraception, 51(5):319–22) (1995).

T lymphocyte associated elastase was reported by Bristow et al., as a protease involved in HIV infection and synthetic elastase inhibitors MAAPVCK but not FLGFL were shown to interfere with HIV infection (Bristow, et al., "*Inhibition of HIV-1 by modification of a host membrane protease*", Int Immunol, 7(2):23949) (1995).

Human proteases PC6A and PC6β isomers were also proposed as gp160 processing enzymes (Miranda et al., "*Isolation of the human PC6 gene encoding the putative host protease for HIV-1 gp160 processing in CD4+ T lymphocytes*", Proc Natl Acad Sci USA, 93(15):7695–700) (1996).

A major serine protease found in plasma, adequately called plasmin, was recently found to be involved in gp160 cleavage (Okumura et al., "*The extracellular processing of HIV-1 envelope glycoprotein gp160 by human plasmin*", FEBS Lett, 442(1):39–42) (1998).

The V3 loop of gp120 was found to be homologous with trypstatin and peptides mimicking V3 region were found to inhibit HIV infection (Cox et al., "*Synergistic combinations and peptides in the inhibition of human immunodeficiency virus*", Adv Enzyme Regul, (31:85–97) (1991).

Several other cellular endoproteases were proposed in the course of the last few years to be involved with HIV but their identity is still unknown (Bukrinskaia et al., "*Inhibition of HIV reproduction in cultured cells using proteolysis inhibitors*", VoprVirusol, 34(1):53–5 (1989); Avril et al., "*Interaction between a membrane-associated serine proteinase of U-937 monocytes and peptides from the V3 loop of the human immunodeficiency virus type 1 (HIV-1) gp120 envelope glycoprotein*", FEBS Lett, 317(1–2):167–72 (1993); Bourinbaiar, et al., "*Effect of serine protease inhibitor, N-alpha-tosyl-L-lysyl-chloromethyl ketone (TLCK), on cell-mediated and cell-free HIV-1 spread*", Cell Immunol, 155(1):230–6 (1994); Schwartz, et al., "*Antiviral activity of the proteasome on incoming human immunodeficiency virus type 1*", J Virol, 72(5):3845–50) (1998).

Thus the list of serine proteases as HIV facilitating enzymes has gradually increased and today in addition to TL2 it includes an assortment of enzymes including furin, kexin, convertase, cathepsin G, subtilisin, subtilisin-like proteases, tryptase M, acrosin, PACE4, PC5/6-B, PC1, VEM, etc.

Although mainstream AIDS research is still concentrated on inhibitors of HIV encoded aspartyl protease, considerable work is being conducted primarily aimed at identifying host cellular endoproteases. While some earlier reports identifying various proteases such as Kunitz type tryptase TL2 seem to have been confirmed, other enzymes as facilitators of HIV infection failed to pass rigorous scientific scrutiny.

For example, furin was found important but not essential for the proteolytic maturation of gp 160 of HIV-1 (Ohnishi et al., "*A furin-defective cell line is able to process correctly the gp16 of human immunodeficiency virus type J*", J. Virol, 68(6):4075–99 (1994); Gu et al., "*Furin is important but not essential for the proteolytic maturation of gp160 of HIV-1*", FEBS Lett, 365(1):95–7) (1995); Inocencio et al.,"*Endoprotease activities other than furin and PACE4 with a role in processing of HIV-1 gp160 glycoproteins in CHO-K1 cells*", J Biol Chem, 272(2):1344–8) (1997).

Similarly, the inhibition of HIV with saliva-derived SLPI as originally reported by McNeely et al., was not supported by subsequent research in several independent labs (Turpin et al., "*Human immunodeficiency virus type-1 (HIV-1 ) replication is unaffected by human secretory leukocyte protease inhibitor*", Antiviral Res, 29(2–3):269–77 (1996); Kennedy et al., "*Submandibular salivary proteases: lack of a role in anti-HIV activity*", J Dent Res, 77(7):1515–9) (1998).

The anti-HIV effect of AAT as speculated by Lezdey et al., (U.S. Pat. No. 5,532,215, incorporated herein by reference in its entirety) was also not confirmed by actual experimental studies carried out by practitioners in the art. Two separate studies, one conducted by Anderson et al., (J Biol Chem, 268(33):24887–91 (1996); and other by Vollenweider et al., (Biochem J, 314 (Pt 2):521–32) (1996), have convincingly demonstrated that naturally occurring or non-mutated AAT directed against its natural substrate, elastase, has not shown any anti-HIV activity. Similarly Harvima et al., have shown that putative tryptase receptors on T lymphocytes were not reactive with anti human anti-tryptase antibody (Harvima et al., "*Separation and partial charac-* terization of proteinases with substrate specificity for basic amino acids from human MOLT-4 T lymphocytes: identification of those inhibited by variable-loop-V3 peptides of HIV-1 (*human immunodeficiency virus*-1) *envelope glycoprotein*", Biochem J, 292 (Pt 3):711–8) (1993). Furthermore, Meylan et al., stated that AAT natural substrates such as trypsin, factor Xa, and mast cell tryptase did not enhance the HIV infectivity (Meylan et al., "*HIV infectivity is not augmented by treatment with trypsin, Factor Xa or human mast-cell tryptase*", AIDS, 6(1):128–30) (1992).

As a result of enzyme studies pertaining to HIV replication, numerous serine protease inhibitors were identified. These include transition state analog peptides such as decanoyl-Arg-Lys-Arg-Arg-psi [CH2NH]-Phe-Leu-Gly-Phe-NH2, substrate analogues such as decanoyl-RVKR-chloromethylketone, suicide substrates such as diisopropyl fluorophosphate (DFP), microbial inhibitors like leupeptin and antipain, leech-derived recombinant tryptase inhibitor (Auerswald et al., "*Recombinant leech-derived tryptase inhibitor: construction, production, protein chemical characterization and inhibition of HIV-1 replication*", Biol Chem Hoppe Seyler, 375(10):695–703) (1994), eglin, trypsin-type protease inhibitors aprotinin, HI-30, E-64, trypstatin, bikunin, H130, N-alpha-tosyl-L-lysyl-chloromethyl ketone, aryl guanidinobenzoates, MG132, and lactacystin (a a complete list of inhibitors can be gleaned from the references identified supra, which are herein incorporated by reference in their respective entireties). Yet, despite all these efforts not a single compound has been considered as clinically acceptable. This is mainly due to the fact that serine protease inhibitors in general have a broad inhibitory range not only toward HIV facilitating enzymes but also against vital proteolytic enzymes that are necessary for a normal function of a host.

In the course of the AIDS progression, many measurable clinical parameters including AAT progressively increase (Cordiali Fei et al., "*Behavior of several 'progression markers' during the HIV-Ab seroconversion period. Comparison with later stages*", J Biol Regul Homeost Agents, 6(2) ;57–64) (1992). AAT was positive in 40% of HIV-positive patients with cryptosporidial infections and none of 12 HIV-positive patients with non-cryptosporidial diarrhea (Lima et al., "*Mucosal injury and disruption of intestinal barrier function in HIV-1-infected individuals with and without diarrhea and cryptosporidiosis in northeast Brazil*", Am J Gastroenterol, 92(10):1861–6) (1997). Scrum concentrations of a tumor-associated trypsin inhibitor (TATI) were very high in some HIV positive subjects and especially in AIDS patients (Banfi et al., "*Tumor-associated trypsin inhibitor in induced and acquired immunodeficiency. Studies on transplanted and HIV-infected patients*", Scand J Clin Lab Invest Suppl, 207:55–8 (1991)). The incidence of abnormal AAT phenotypes was 16.3% in the homosexual group which was significantly different (p less than 0.03) than the 8.7% in the heterosexual group. There was no difference in the phenotype distribution between homosexuals who were anti-HIV antibody reactive and those who were non-reactive (Deam et al., "*Alpha* 1-*antitrypsin phenotypes in homosexual men*", Pathology, 21(2):91–2) (1989). Faecal alpha1 antitrypsin concentration were reflective of abnormal pancreatic function of paediatric HIV infection (Carroccio et al., "*Pancreatic dysfunction and its association with fat malabsorption in HIV infected children*", Gut, 43(4):55863) (1998). Patients with HIV-1 infection are known to acquire an obstructive pulmonary disease with clinical similarity to emphysema. AAT levels measured in these patients were in the lower normal range. Despite observing these clinical findings in 42% of consecutive HIV-1-infected patients in the clinic, no evidence of current of previous opportunistic infection was detected. Bronchoalveolar lavage fluid obtained in a subset of these patients contained TNF and free radicals, indicating inflammation. It is possible that HIV-1 associated free radical production inactivated pulmonary AAT and facilitated the development of the cryptogenic emphysema-like condition.

Also, high levels of serum trypsin and elastase are present in an elevated percentage of patients with AIDS, suggesting that the pancreas is frequently damaged in this disease. A significant inverse relationship was found between serum enzyme concentrations and the number of CD4+ lymphocytes (Pezzilli et al., "*Serum pancreatic enzymes in HIV-seropositive patients*", Dig Dis Sci, 37(2):286–8) (1992).

In vitro studies have shown that HIV-1 was found sensitive to inactivation by low concentrations of trypsin (Tang et al., "*Inactivation of HIV-1 by trypsin and its use in demonstrating specific virus infection of cells*", J Virol Methods 33(1–2):3946) (1991). This led to the belief that trypsin therapy might be useful to treat HIV. Chymotrypsin and trypsin manufactured in the former USSR in doses of 10 mg each administered intramuscularly appeared to normalize the abnormal, reduced ratio of CD4/CD8 cells—a condition observed in persons infected with the HIV (Glozman, "*Immunologic foundation of enzyme therapy of patients with orchiepididymitis*", Antibiot Khimioter, 35(7):50–2) (1990).

Prior to the present invention it was generally believed that the naturally occurring serine protease inhibitor AAT was ineffective against HIV infection. Alternatively, prior to the present invention it was speculated that AAT might be useful for inhibition of HIV proliferation by blocking HIV encoded aspartyl protease or a similar cellular protease that mediate gag-pol cleavage. The present inventor has discovered that, contrary to these earlier convictions, naturally occurring AAT and derivatives thereof are useful for inhibition of HIV via several unexpected modes of action not recognized in the prior art.

It is therefore the goal of the present invention, in its broadest aspect, to provide methods of treating diseases dependent on the action of protease inhibitors. Accordingly, it should be recognized that this invention is applicable to the control of catalytic activity of serine proteases in any appropriate situation including, but not necessarily limited to, medicine, biology, agriculture, and microbial fermentation. These and other objects and advantages of the present invention will be recognized by those skilled in the art from the following description and representative examples.

It is therefore the overall object of the present invention to provide compounds, which exhibit inhibitory activity toward serine proteases.

It is an object of the present invention to provide clinically acceptable serine protease inhibitors with recognized utility and exhibiting relatively high activity at relatively low concentrations.

It is another object of the present invention to provide serine protease inhibitors exhibiting selectivity for certain key proteases involved in viral activation and infection. It is yet another object of the invention to provide means of regulating virus release by compounds having AAT activity either alone or in combination with other anti-HIV compounds.

These and other objects and advantages of the present invention will be recognized by those skilled in the art from the following description and illustrative examples.

The present invention offers useful insight into therapy and pathogenesis of viral infection. In particular it provides a method of treating viral infection facilitated or mediated by a serine proteolytic (SP) activity comprising administering to a subject suffering or about to suffer from said viral infection a therapeutically effective amount of a compound having a serine protease inhibitory or serpin activity comprising $\alpha_1$-antitrypsin activity (AAT). The viral infection may include retroviral infection such as human immunodeficiency virus (HIV) infection.

A method of preventing or inhibiting delivery of viral nucleic acid into the nucleus of a mammalian host as well as a method of preventing or inhibiting the exit of a virion particle from a mammalian host harboring an agent of a viral infection is provided. Preferably these processes axe mediated by endogenous host serine protease (SP) or SP-like activity and will be counteracted by administering a pharmacologically effective amount of a substance exhibiting mammalian $\alpha_1$-antitrypsin (AAT) or AAT-like activity. According to this method the post-exposure prophylaxis is contemplated in order to block establishment of productive infection in a mammal exposed to HIV-contaminated fluids such as blood, saliva, semen, sweat, urine, vaginal secretion, tears, and other body fluids that may contain HIV either in cell-free form or in cell-associated from. It also understood that said method is effective in preventing mother-to-child HIV transmission during pregnancy. According to this method pharmacologically effective amount of a substance exhibiting mammalian $\alpha_1$-antitrypsin (AAT) or AAT-like activity incorporated in topical vaginal or rectal formulations as well as in condoms and intrauterine devices (IUD) is useful for preventing sexual transmission of HIV.

Among preferred compounds to treat such viruses is a substantially purified natural or recombinant AAT. AAT and similarly active compounds may be identified by a series of assays wherein a compound (AAT) will exhibit inhibitory activity versus control in an assay. One of these assays comprises blocking interleukin-18 or IL-18-induced human immunodeficiency virus (HIV) production in U1 monocytic cells. Other assays involve blocking stimulants such as IL-6, NaCl, LPS, TNF, and other HIV stimulants known in the art. Other assays involve MAGI-CCR-5 cell assay and PBMC assay as described in detail in the body of the disclosure.

Also contemplated is a series of peptides comprising carboxyterminal amino acid peptides corresponding to AAT. Among this series of peptides, several are equally acceptable including FVFLM (SEQUENCED NO.1), FVFAM (SEQUENCE ID NO.2), FVALM (SEQUENCE ID NO. 3), FVFLA (SEQUENCE ID NO.4), FLVFI (SEQUENCE ID NO.5), FLMII (SEQUENCE ID NO.6), FLFVL (SEQUENCE ID NO. 7), FLFVV (SEQUENCE ID NO.8), FLFLI (SEQUENCE ID NO. 9), FLFFI (SEQUENCE ID NO.10), FLMFI (SEQUENCE ID NO.11), FMLLI (SEQUENCE ID NO.12), FUMI (SEQUENCE ID NO.13), FLFCI (SEQUENCE ID NO.14), FLFAV (SEQUENCE ID NO.15), FVYLI (SEQUENCE ID NO.16), FAFLM (SEQUENCE ID NO.17), AVFLM (SEQUENCE ID NO.18), and combination thereof.

These pentapeptides can be represented by a general formula (I): I-A-B-C-D-E-F-G-H-II, wherein I is Cys or absent; A is Ala, Gly, Val or absent; B is Ala, Gly, Val, Ser or absent; C is Ser, Thr or absent; D is Ser, Thr, Ans, Glu, Arg, Ile, Leu or absent; E is Ser, Thr, Asp or absent; F is Thr, Ser, Asn, Gln, Lys, Trp or absent; G is Tyr or absent; H is Thr, Gly, Met, Met(O), Cys, Thr or Gly; and II is Cys, an amide group, substituted amide group, an ester group or absent, wherein the peptides comprise at least 4 amino acids and physiologically acceptable salts thereof.

The peptides of interest are homologous and analogous peptides. While homologues are natural peptides with sequence homology, analogues will be peptidyl derivatives, e.g., aldehyde or ketone derivatives of such peptides. Typical examples of analogues are oxadiazole, thiadiazole and triazole peptoids. Without limiting to AAT and peptide derivatives of AAT, compounds such as oxadiazole, thiadiazole and triazole peptoids are preferred.

The preferred doses for administration can be anywhere in a range between about 10 ng and about 10 mg per ml of biologic fluid of treated patient. The therapeutically effective amount of AAT peptides or drugs that have similar activities as AAT or peptide drug can be also measured in molar concentrations and may range between about 1 nM and about 1 mM per ml of biologic fluid of treated patient.

It is another object of the present invention to provide pharmaceutical compositions with serine protease inhibiting activity comprising a pharmaceutically acceptable carrier and a therapeutically effective amount of at least one of the compounds of the present invention or a pharmaceutically acceptable salt or prodrug form thereof.

Other viral infections are contemplated to be treated wherein such viral infections are caused/facilitated by a deficiency in AAT levels or by a dysfunction of AAT. Clinical conditions and viral infections resulting from uncontrolled serine protease activity are also within the scope of the present invention and will be treated alike.

A general method of treating a mammal suffering from a pathological condition that is mediated by endogenous serine protease (SP) or SP-like activity is contemplated as well, which comprises administering a therapeutically effective amount of a substance exhibiting mammalian $\alpha_1$-antitrypsin (AAT) or AAT-like activity. This pathological condition can be caused at least in part by a viral infection.

Without limiting to AAT a compound of choice may be one that inhibits proteinase-3, cathepsin G, or elastase.

In accordance with this invention, there is provided a novel class of chemical compounds that are capable of inhibiting and/or blocking the activity of the serine protease (s), which halts the proliferation of a virus including HIV, pharmaceutical compositions containing these compounds, novel intermediates for compounds which inhibit and block the activity of the HIV facilitating serine protease, novel methods for making such compounds, and use of the compounds as inhibitors of the HIV.

It should be apparent that in addition to these preferred embodiments a method is contemplated which consists of treating an individual having a physiological condition caused, in whole or part, by virus shedding. In accordance to this embodiment a method of inhibiting virus release is provided wherein the target of the therapy is a cell and one will contact such cell with an effective amount of a compound having AAT activity.

It is another object of the present invention to provide a novel method for treating HIV infection which comprises administering to a host in need thereof a therapeutically effective combination of (a) one of the compounds of the present invention and (b) one or more compounds selected from the group consisting of HIV reverse transcriptase inhibitors and HIV protease inhibitors. Accordingly reverse transcriptase inhibitor can be selected from a group including nucleoside RT inhibitors: Retrovir (AZT/zidovudine; Glaxo Wellcome); Combivir (Glaxo Wellcome); Epivir (3TC, lamivudine; Glaxo Wellcome); Videx (ddI/didanosine; Bristol-Myers Squibb); Hivid (ddC/zalcitabine; Hoffmann-La Roche); Zerit (d4T/stavudine; Bristol-Myers Squibb); Ziagen (abacavir, 1592U89; Glaxo Wellcome); Hydrea (Hydroxyurea/HO; nucleoside RT potentiator from Bristol-Myers Squibb) or Non-nucleoside reverse transcriptase inhibitors (NNRTIs): Viramune (nevirapine; Roxane Laboratories); Rescriptor (delavirdine; Pharmacia & Upjohn); Sustiva (efavirenz, DMP-266; DuPont Merck); Preveon (adefovir dipivoxil, bis-POM PMEA; Gilead). Protease inhibitors (PI's) are selected from Fortovase (saquinavir; Hoffmann-La Roche); Norvir (ritonavir; Abbott Laboratories); Crixivan (indinavir; Merck & Company); Viracept (nelfinavir; Agouron Pharmaceuticals); Angenerase (amprenavir/141W94; Glaxo Wellcome), VX-478, KNI-272, CGP-61755, and U-103017.

Also contemplated is a method of preventing acquired or congenital deficiency of functional we endogenous AAT levels in a patient susceptible to a viral infection that is mediated by endogenous host serine protease (SP) or SP-like activity by treating the patient with a pharmaceutical composition in a pharmaceutically acceptable carrier comprising an effective amount of a substance exhibiting mammalian $\alpha_1$-antitrypsin (AAT) or AAT-like activity and a thrornbolytic agent such as tissue plasminogen activator, urokinase, streptokinase, or combinations or complexes thereof. The pharmaceutical composition may be a peptide or a small molecule, which exhibits AAT or AAT-like activity.

The treatment and prevention of virus induced tumors by administering $\alpha_1$-antitrypsin (AAT) or a compound with AAT-like activity is another object of this invention. Yet another preferred embodiment of this invention is to provide $\alpha_1$-antitrypsin (AAT) or a compound with AAT-like activity for types of cancer that may or may not be virus induced but are capable of metastasizing due to SP activity. Such tumors may comprise fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, melanoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, neuroblastoma, retinoblastoma, myeloma, lymphoma, and leukemia.

DETAILED DESCRIPTION OF THE INVENTION

Figure 1:
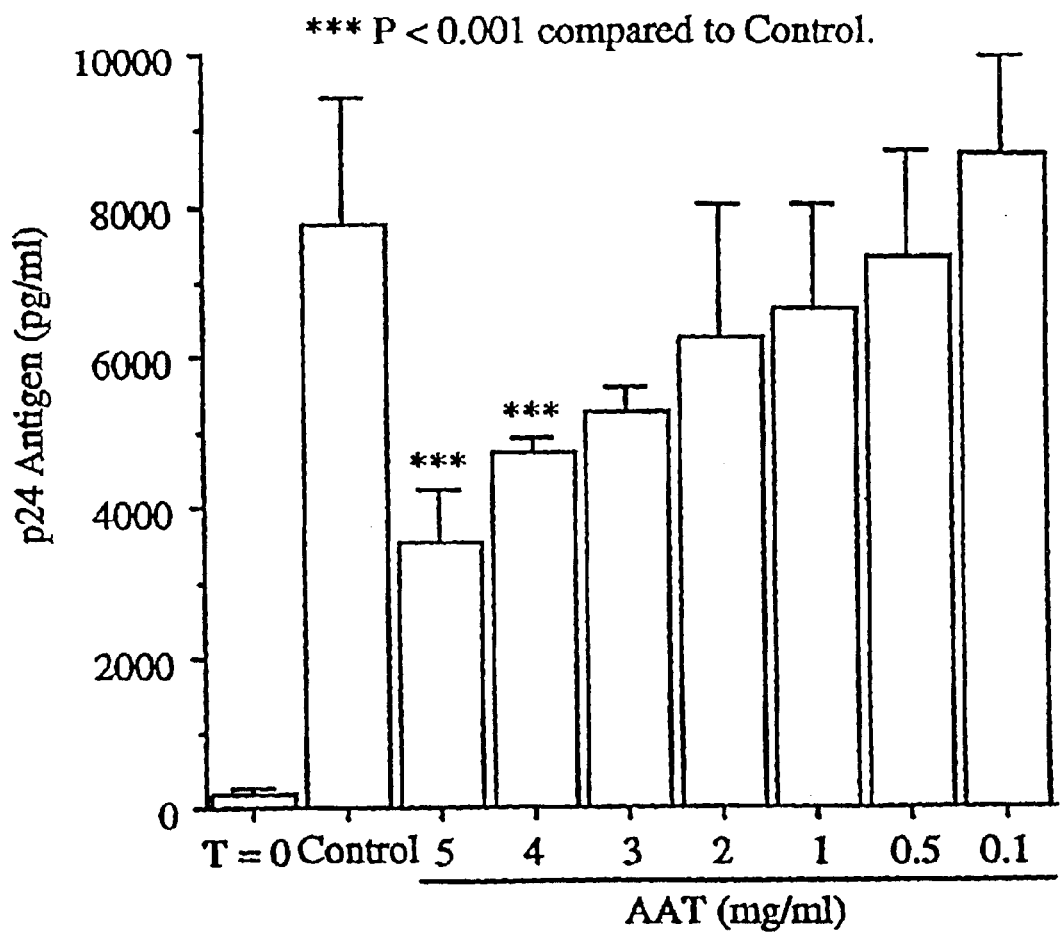
FIG. 1 illustrates the effect of AAT on HIV production in PBMC as performed without pre-incubation.

The present invention provides a method of treatment that is totally opposite to the prevailing therapeutic approaches and provides enzyme antagonist instead of a trypsin-like enzyme.

Throughout this application various publications and patents are referenced. The disclosures of these publications and patents in their entireties are hereby incorporated by reference into this application in order to more fully describe the state of the art to which this invention pertains.

AAT preparations of the instant invention can be obtained by a variety of methods. For example, U.S. Pat. Nos. 5,529,920 to Cole et al., and 5,665,589 Harris et al., disclose liver-derived cell lines producing AAT. U.S. Pat. Nos. 5,861,299 to Archibald et al., 5,780,009 Karatzas et al., and 5,476,995 to Clark et al., disclose methods of obtaining transgenic AAT from the milk of transgenic mammals (cows, goats, sheep, pigs, etc.) as a source of AAT. U.S. Pat. Nos. 4,839,283 to Kawasaki et al., 5,593,858 to Fleer et al., 5,641,670 to Treco et al., and 5,565,334 to Kufe et al., disclose various recombinant methods of wild type AAT production (wild type refers to AAT which is essentially identical to one found in human plasma). U.S. Pat. Nos. 5,604,201 to Thomas et al., 4,732,973 to Barr et al., and 5,817,484 to Yu et al., disclose recombinant mutant AAT variants from cells transformed by recombinant DNA technology.

The peptide-based serine protease inhibitors may be prepared by any suitable synthesis method such as originally described by Merrifield, J. Am. Chem. Soc. Vol. 85, p. 2149 (1963). Synthetic peptides, which exhibit inhibitory activity toward serine proteases and methods for preparing and using the same are disclosed for example in U.S. Pat. Nos. 4,829,052, 5,157,019 to Glover; U.S. Pat. No. 5,420,110 to Miller; U.S. Pat. No. 4,963,654 to Katunuma, and incorporated herein by reference. Those skilled in the art of biochemical synthesis will recognize that for commercial-scale quantities of peptides, such peptides can also be prepared using recombinant DNA techniques.

It is to be understood that the present invention is not limited to the examples described hereinabove and other serine protease inhibitors known in the art can be used within the limitations of the invention. For example, one skilled in the art can easily adopt inhibitors as described in WO 9824806, which discloses substituted oxadiazole, thiadiazole and triazole as serine protease inhibitors. U.S. Pat. No. 5,874,585 discloses substituted heterocyclic compounds useful as inhibitors of serine proteases; U.S. Pat. No. 5,869, 455 discloses N-substituted derivatives; U.S. Pat. No. 5,861, 380 discloses protease inhibitors-keto and di-keto containing to ring systems; U.S. Pat. No. 5,807,829 discloses serine protease inhibitor—tripeptoid analogues; U.S. Pat. No. 5,801,148 discloses serine protease inhibitors-proline analogues; U.S. Pat. No. 5,618,792 discloses substituted heterocyclic compounds useful as inhibitors of serine proteases. In addition, European patents exist such as EP0886647 disclosing serine protease inhibitors; EP0786996 disclosing cysteine protease and serine protease inhibitors; EP0764151 disclosing purification of serine protease and synthetic inhibitors thereof; EP0765342 disclosing methods of producing effective recombinant serine protease inhibitors and uses of these inhibitors; EP0788546 disclosing nematode-extracted serine protease inhibitors and anticoagulant proteins; EP0871454 disclosing phosphorous-containing cysteine and serine protease inhibitors.

The above patents and PCT publications listed infra are enclosed herein by way reference. Other equally advantageous molecules, which may be used instead of AAT or in combination with AAT are contemplated such as in WO 98/20034 disclosing serine protease inhibitors from fleas. Without limiting to this single reference one skilled in the art can easily and without undue experimentation adopt compounds such as in WO98/23565 which discloses aminoguanidine and alkoxyguanidine compounds as useful for inhibiting serine proteases; WO98/50342 discloses bis-aminomethylcarbonyl compounds useful for treating cysteine and serine protease disorders; WO98150420 cyclic and other amino acid derivatives useful for thrombin-related diseases; WO 97/21690 D-amino acid containing derivatives; WO 97/10231 ketomethylene group-containing inhibitors of serine and cysteine proteases; WO 97/03679 phosphorous containing inhibitors of serine and cysteine proteases; WO 98/21186 benzothiazo and related heterocyclic inhibitors of serine and proteases; WO 98/22619 discloses a combination of inhibitors binding to P site of serine proteases; WO 98/22098 a composition which inhibits conversion of pro-enzyme CPP32 subfamily including caspase 3 (CPP321Yama/Apopain); WO 197/48706 pyrrolo-pyrazine-diones; WO 97/33996 human placental bikunin (recombinant) as a serine protease inhibitor; WO 98/46597 complex amino acid containing molecules for treating viral infections and conditions disclosed hereinabove.

The compounds of the present invention are used as therapeutic agents in the treatment of a physiological (especially pathological) condition caused in whole or part, by uncontrolled serine protease activity. The peptides may be administered as free peptides or pharmaceutically acceptable salts thereof. The terms used herein conform to those found in Budavari, Susan (Editor), "The Merck Index" An Encyclopedia of Chemicals, Drugs, and Biologicals; Merck & Co., Inc. The term "pharmaceutically acceptable salt" refers to those acid addition salts or metal complexes of the peptides which do not significantly or adversely affect the therapeutic properties (e.g. efficacy, toxicity, etc.) of the peptides. The peptides should be administered to individuals in need thereof as a pharmaceutical composition, which, in most cases, will comprise the peptide and/or pharmaceutical salts thereof with a pharmaceutically acceptable carrier. The term "pharmaceutically acceptable carrier" refers to those solid and liquid carriers, which do not significantly or adversely affect the therapeutic properties of the peptides. The pharmaceutical compositions containing peptides of the present invention may be administered to individuals, particularly humans, either intravenously, subcutaneously, intramuscularly, intranasally or even orally. The necessary dosage will vary with the particular condition being treated, method of administration and rate of clearance of the peptide from the body. In most cases dosages between 0.001 and 30 mg/kg are effective. A dose range between 0.1 and 10 mg/ml of bodily fluid, such as blood, plasma, serum, semen, mucosal secretion, or saliva is preferred. Concentrations as expressed in molar units will vary accordingly depending on molecular weight of a given compound and adjustments to that effect are within the skill of a practitioner.

Routes of administration include, but are not limited to, topical, transdermal, parenteral, gastrointestinal, transbronchial and transalveolar. Topical administration is accomplished via a topically applied cream, lotion, emulsion, gel, suppository, pessary, tablet, sachet, spray, rinse, etc. containing therapeutically effective amounts of serpins. Topical routes are vaginal, rectal, nasal, sublingual, ocular, etc., and which are either transmucosal or transdermal means of delivery. Transdermal administration is accomplished by application of a cream, rinse, gel, etc. capable of allowing the serpins to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally and direct injection into an airway, such as through a tracheotomy.

Although the compounds described herein and/or their derivatives may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefor and, optionally, other therapeutic and/or prophylactic ingredients. The carrier(s) must be acceptable in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets, each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or another suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampoules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the delivery system can be in slow release sustained form known in the art.

The above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, perfumes, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, the compound is conveniently administered in unit dosage form; for example, containing 5 to 2000 mg, conveniently 10 to 1000 mg, most conveniently, 50 to 500 mg of active ingredient per unit dosage form.

Ideally, the active ingredient should be administered to achieve peak plasma concentrations of the active compound of from about 100 ng to 10 mg, preferably, about 1 microgram to 5 mg most preferably, about 2 to about 4 mg per ml of plasma fluid. This may be achieved, for example, by the intravenous injection of a 0.05 to 5% solution of the active ingredient, optionally in saline, or orally administered as a bolus containing about 10–1000 mg of the active ingredient. Desirable blood levels may be maintained by continuous infusion to provide about 0.01–5.0 mg/kg/hr or by intermittent infusions containing about 0.4–20 mg/kg of the active ingredient(s). Buffers, preservatives, antioxidants and the like can be incorporated as required. The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

EXAMPLES

Example 1

General Procedure and Materials

Alpha-1-antitrypsin (AAT) used in these studies is purified from the blood of healthy volunteers. AAT is purified to single-band homogeneity. The AAT protein is diafiltered into a diluent consisting of NaCl, sodium phosphate, pH 7.05. The AAT preparations are maintained at stock concentrations of 14–50 mg/ml and stored at −70° C. until added to cultures. As a control AAT preparation that is different from the composition of the invention a commercially available Prolastin (Bayer's AAT) is used. Recombinant human interleukin (IL)-18 is obtained from Vertex Pharmaceuticals Inc., (Cambridge, Mass.). IL-6 and tumor necrosis factor (TNF) are obtained from R & D Systems, Minneapolis, Minn., endotoxin-free NaCl, and endotoxin (lipopolysaccharide, LPS) is obtained from Sigma (St. Louis, Mo.).

Medium for monocytic U1 cell and MAGI-CCR5 cell cultures consists of RPMI 1640 medium purchased from Mediatech (Herndon, Va.) containing 2.5 mM L-glutamine, 25 mM Hepes, 100 units/ml penicillin and streptomycin (GIBCO/BRL, Rockville, Md.) with 10% or 7.5% (vol/vol) heat-inactivated fetal bovine serum (FBS, GIBCO) for U1 cell and MAGI-CCR5 cell cultures, respectively. PBMC are cultured in R3 medium consisting of RPMI 1640 medium (Mediatech), 20% FBS (GIBCO), 100 units/ml penicillin and streptomycin (GIBCO) and 5% (vol/vol) IL-2 (Hemagen, Waltham, Mass.).

U1 monocytic cell assay. U1 cells are obtained from the AIDS Research and Reference Reagent Program, National Institute of Allergy and Infectious Diseases, NIH. U1 cells are maintained in T-175 polystyrene flasks (Falcon, Becton Dickinson, Franklin Lakes, N.J.) in medium and used when in log phase growth. Cells are counted in a hemacytometer, examined for viability by Trypan blue exclusion (>95% for all experiments) and resuspended in fresh medium at $2 \times 10^6$ per ml. Two-hundred fifty ml of cell suspension are added to wells of 24-well polystyrene tissue culture plates (Falcon), followed by the addition of medium or AAT to produce the final concentration to be tested in a volume of 450 ml. After 1.0 hr of incubation (37° C., 5% $CO_2$), 50 ml of medium (control) or stimulus diluted in medium are added to wells to produce the final concentration of stimulus to be tested. The final culture volumes are 500 ml and contained $1 \times 10^6$ cells per ml. After 48 hr of incubation (37° C. and 5% $CO_2$) 50 ml of 10% (vol/vol) Triton-X-100 (Fisher Scientific, Fair Lawn, N.J.) is added to each culture (final concentration of 1% vol/vol), and cultures are frozen and thawed once. This is followed by assay for HIV-1 p24 antigen by ELISA with a lower limit of detection of 31 pg/ml (NCI-Frederick Cancer Research and Development Center, Frederick, Md.). The disruption of cells due to the addition of Triton-X-100 and the freeze-thaw cycle produced cell lysates and enabled assessment of total (secreted and cell-associated) production of p24 antigen. Peripheral Blood Mononuclear Cells (PBMC) based HIV assay.

These studies are approved by the Combined Investigation Review Board of the University of Colorado Health Sciences Center. PBMC from HIV-1 negative healthy subjects are isolated from heparinized blood by Ficoll-Hypaque density-gradient centrifugation. The concentration of PBMC in aliquots are counted using a hemacytometer (viability>95% by trypan blue exclusion for each experiment) and PBMC are diluted at $1 \times 10^6$ per ml in R3 medium supplemented with additional 5% (vol/vol) 12 and 3.3 mg/ml phytohemagglutinin (PHA, Sigma). Cell suspensions are then incubated for 2 days (37° C., 5% $CO_2$) in T-175 polystyrene tissue culture flasks (Falcon).

The stocks of lymphocyte-tropic HIV-1 strain A018A are titered by standard protocol and are used to infect PBMC. Following the 2 days of incubation, PBMC from each donor are removed from tissue culture flasks, divided into 2 equal aliquots placed into 50 ml polypropylene tubes (Falcon), concentrated by centrifugation and the medium decanted. Each parallel aliquot is infected by incubation with 300 tissue culture infective doses (TCID), HIV-1 per $1 \times 10^6$ cells for 3 hr in 500 ml medium. The parallel PBMC infections from each donor are conducted in the absence or presence of 3 mg/ml AAT. The infected PBMC (without or with 3.0 mg/ml AAT) are then resuspended and washed in 15 ml R3 medium, pelleted, and resuspended at $2 \times 10^6$ per ml in fresh R3 medium. Two hundred fifty ml of HV-1-infected PBMC is aliquoted into 24-well polystyrene tissue culture plates (Falcon). An additional 250 ml R3 medium (control) or AAT is added to appropriate wells to produce a final culture volume of 500 ml containing $1 \times 10^6$ cells per ml. For each donor, a separate 250 ml aliquot of PBMC suspension is added to a 1.5 ml polypropylene microfuge tube (Fisher) along with 200 ml R3 medium and 50 ml of 10% (vol/vol) Triton-X-100 (Fisher). This sample is frozen and designated time 0. Cultures in 24-well plates are incubated for 4 days, after which Triton-X-100 (Fisher) is added (final concentration of 1% vol/vol as described above for U1 cell cultures) and plates frozen and thawed once. Corresponding time 0 samples are thawed with each plate and cell lysates assayed for p24 antigen by ELISA.

MAGI-CCR5 cell assay.

The MAGI (Multinuclear Activation of a Galactosidase Indicator)-CCR-5 cell line is a clone derived from the HeLa cell line that expresses high levels of CD4. It has been transfected with a single integrated copy of a galactosidase gene under control of the HIV-1 long terminal repeat. Beta-galactosidase is expressed upon production of HIV-1 Tat protein following one round of HIV-1 replication within the cell. The MAGI-CCR-5 cell line is derived from MAGI cells into which the CCR-5 HIV-1 co-receptor gene has been incorporated. These cells constitute an assay for early infection events and can be infected with either lymphocyte-tropic or macrophage-tropic HIV-1 strains. MAGI-CCR-5 cells are obtained from the AIDS Research and Reference Reagent Program, National Institute of Allergy and Infectious Diseases, NIH. Cells are cultured in polystyrene T-175 flasks (Falcon) in medium until cells are noted to be in Aa log growth phase. Cells are then resuspended in fresh medium and aliquoted into 24-well polystyrene plates (Falcon) at $4 \times 10^4$ cells per well (1 ml total volume). After 24 hr incubation adherent cells are 30–40% confluent and all medium is removed. Two hundred ml of fresh medium is then added to each well without (negative control) or with AAT and incubated for 1 hour. AAT diluent is added to a separate well at a volume equivalent to that of the highest concentration of AAT tested (control).

One hundred thirty $TCID_{50}$ of HIV-1 and DEAE dextran in medium are added to each well. T-cell tropic HIV-1 strain A018A is used. After 2 hr incubation, medium is added to each well to adjust the final volume of each well to 500 ml. Cultures are incubated for 48 hr, which allows infection of the MAGI-CCR-5 cells. Medium is aspirated and the cells fixed for 5.0 min at room temperature by adding 1.0 ml of a 1% formaldehyde/0.2% glutaraldehyde solution in phosphate buffered saline (PBS). Fixing solution is then aspirated and cells washed with PBS. This is followed by addition of galactosidase staining solution. Fifty min of incubation is followed by a blinded optical count of pigmented cells under a microscope.

Statistical Analysis.

Data are presented as means±SEM. Group means are compared by ANOVA using Fisher's least significant difference. For data expressed as percent change, the values for p24 in control cultures (medium alone) are subtracted from those for each culture-containing stimulus. The p24 concentrations in cultures conducted in the presence of stimulus alone are set at 100%. Percent p24 in cultures containing stimulus and AAT are calculated by dividing the measured p24 by that present in cultures containing stimulus alone. The resultant fraction is expressed as a percent.

Example 2

Anti-HIV effect of AAT

AAT Inhibits Production of HIV-1 in U1 Cell Cultures.

The U1 cell line is derived from human monocytic U937 cells into which 2 copies of HIV-1 provirus are incorporated into host genome. Exposing U1 cells to pro-inflammatory cytokines such as IL-18, IL-1, IL-6 and TNF, phorbol esters or hyperosmolarity results in the induction of HIV-1 as assessed by p24 antigen. Stimulation of U1 cells with 0.5 nM IL-18 induced large amounts of p24 antigen after 48 hr of incubation in 3 separate experiments. U1 cells cultured in medium alone (control) contained a mean of 41.3±11.5 pg/ml p24 antigen, which is increased 150-fold to 6,235 t 1,775 pg/ml p24 following stimulation with IL-18. Cultures conducted in the presence of AAT added 1 hour prior to the addition of IL-18 demonstrated a dose-dependent reduction in p24, with near ablation of IL-18-induced p24 observed at 3 mg/ml AAT. AAT added at 0.1, 0.5, 1,2 and 3 mg/ml resulted in 6,879±207, 3,687±968, 2.029±625, 452±209 and 179±79 pg/ml p24 production, respectively. At 1, 2 and 3 mg/ml AAT, the percent reductions observed compared to stimulation with IL-18 alone are 65±1.8, 93±3.0 and 98±1%, respectively.

Figure 13:
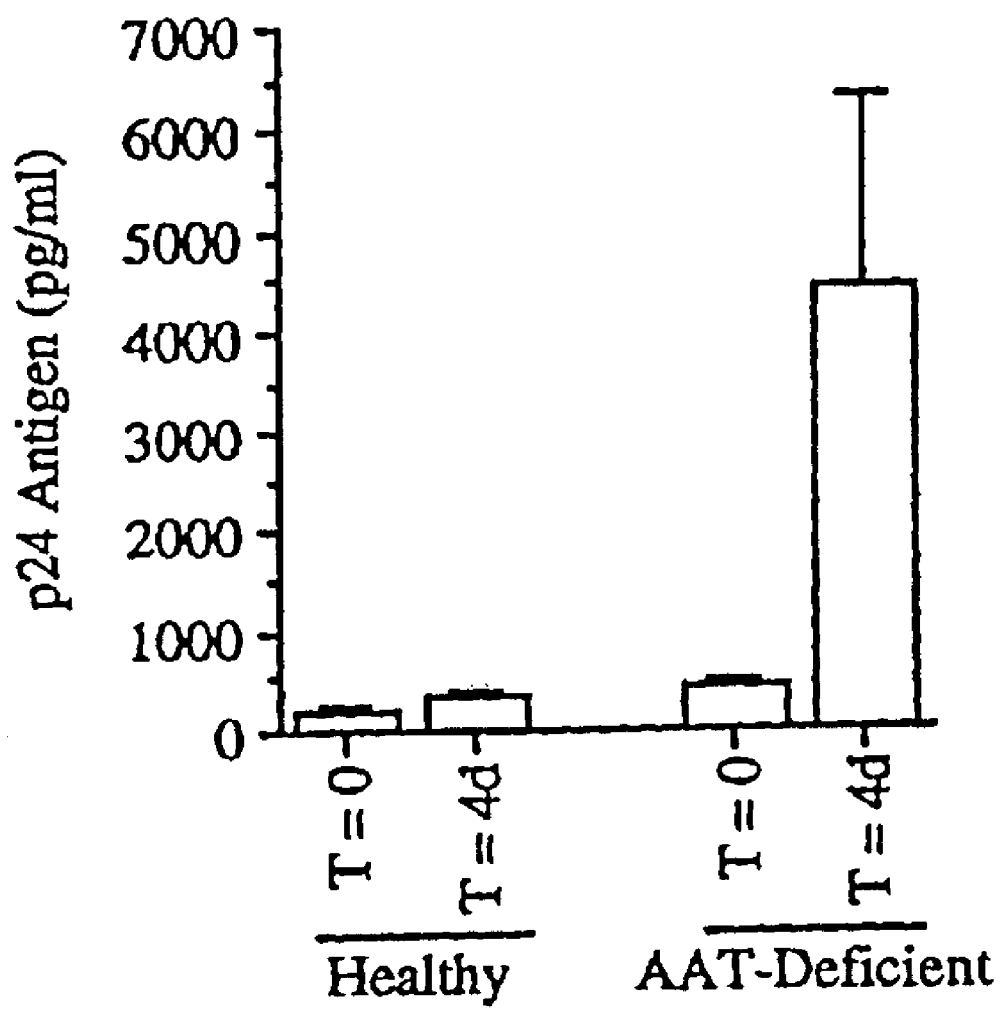
FIG. 13 illustrates the p24 antigen output of HIV when grown in normal or AAT-deficient whole blood.
Figure 14:
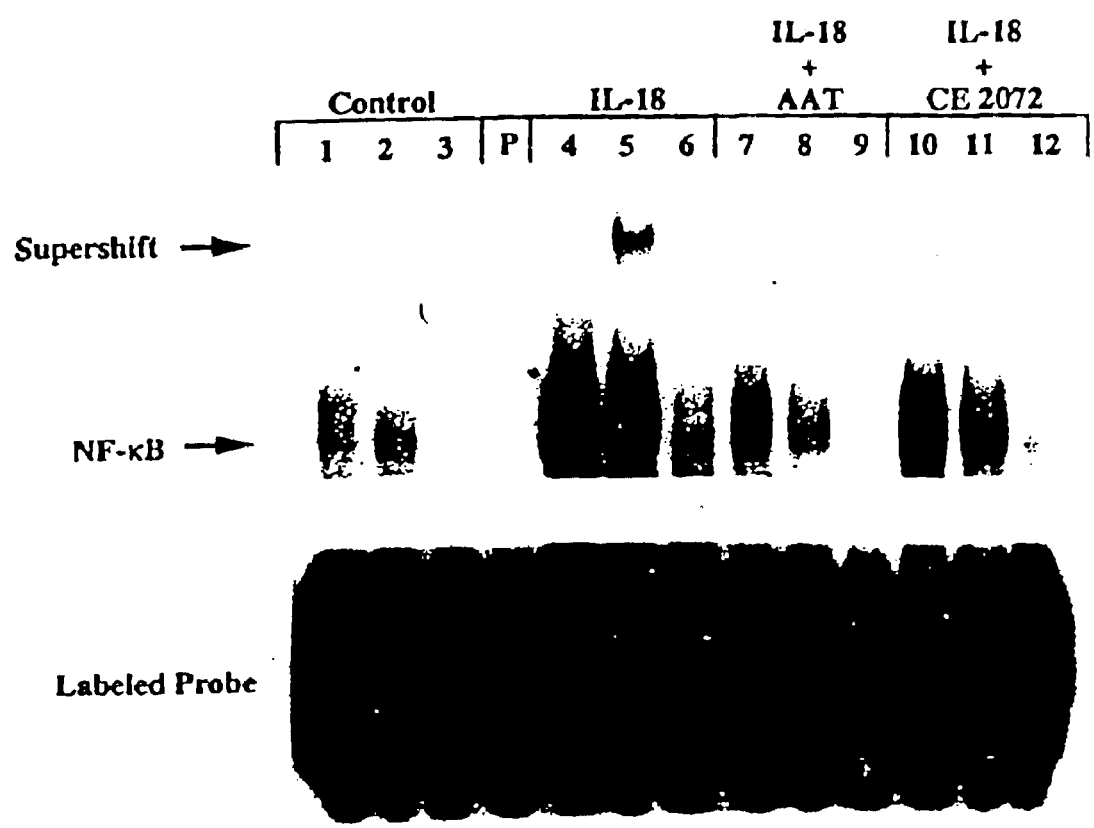
FIG. 14 illustrates the effect of AAT and AAT-mimicking drug (CE 2072) in reducing IL-18induced NF-κB activation.

To evaluate the effect of AAT on U1 cell proliferation and viability, 3 experiments are performed in the presence or absence of 5 mg/ml AAT. U1 cells are added at $1 \times 10^6$ cells per ml and cultured for 48 hrs. Following incubation, cells are quantified using a hemacytometer. The mean±SEM cell concentrations in control and AAT-containing cultures are $2.5 \times 10^6 \pm 0.5 \times 10^6$ and $2.4 \times 10^6 \pm 0.3 \times 10^6$ respectively. These values are each significantly higher than the $1 \times 10^6$ cells per ml added initially (P<0.05), but they are not significantly different from one another. For all cultures, cell viability by trypan blue exclusion is >95%. The lack of toxicity is illustrated in FIG. 13.

Figure 7:
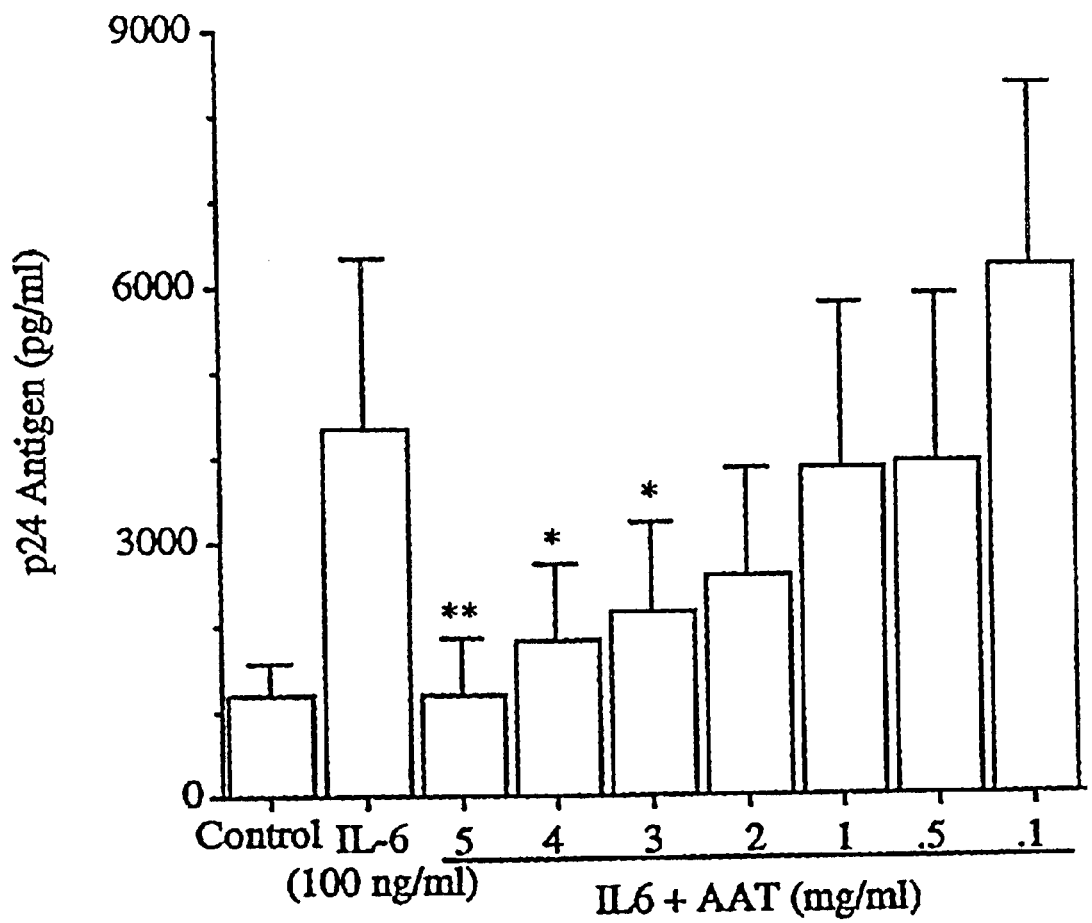
FIG. 7 illustrates the effect of AAT on HIV production in U1 cells upon induction with IL-6.

In 4 separate experiments, using 100 ng/ml IL-6 as a stimulus, the mean p24 antigen measured in U1 cells cultured in medium alone (control) is 1,207±361 pg/ml (FIG. 7). Stimulation with 100 ng/ml IL-6 results in a 3.6-fold increase in p24 antigen production, to 4,337±2,006 pg/ml. Stimulation with IL-6 in the presence of AAT results in dose-dependent inhibition of p24 production compared to that measured in the absence of AAT. With the addition of AAT at 0.1, 0.5, 1, 2, 3, 4, and 5 mg/ml, the measured P24 antigen values are 6,228±2,129, 3,992±1,987, 3,850±1,943, 2,597±1,253, 2,155±1,085, 1,838±881 and 1,213±658 pg/ml, respectively. The corresponding mean percent reductions for AAT additions of 3, 4 and 5 mg/ml are 80, 88 and 100%, respectively.

Figure 8:
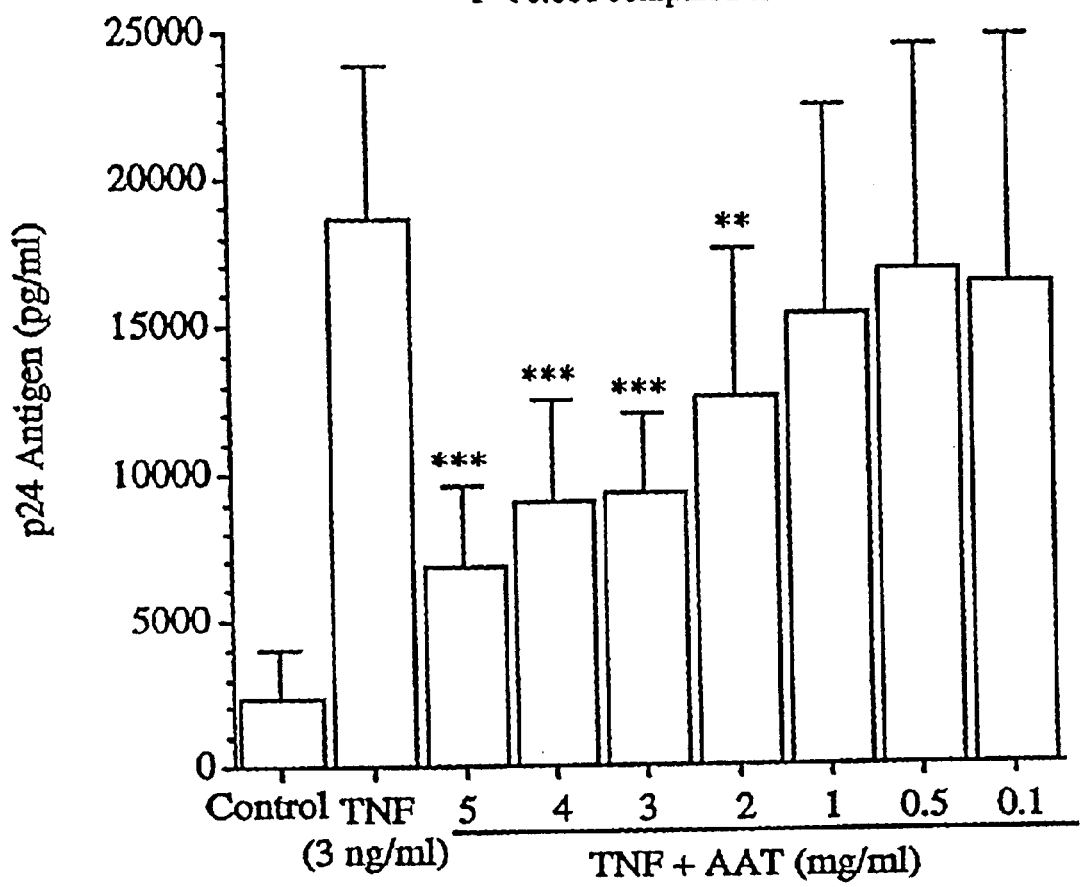
FIG. 8 illustrates the effect of AAT on HIV production in U1 cells upon induction with TNF.

In 4 separate experiments, obtained in U1 cells exposed to TNF as stimulus, the mean p24 antigen measured in control and TNF-stimulated (3.0 ng/ml) cultures are 2,328±1,680 and 18,635±5,243 pg/ml, respectively (FIG. 8). This 8-fold increase in p24 production is significantly and dose-dependently reduced in the presence of AAT. Inclusion of AAT at the concentrations 0.1, 0.5, 1, 2, 3, 4, and 5 mg/ml reduced TNF-induced p24 antigen to 16,405±8,449, 16,863±7,718, 15,328±7,129, 12,566±4,981, 9,341±2,730, 9,091±3,436 and 6,868±2,737, respectively. The mean percent reductions in TNF-induced p24 antigen observed in the presence of 3, 4, and 5 mg/ml AAT are 56, 60, and 73%, respectively.

Figure 9:
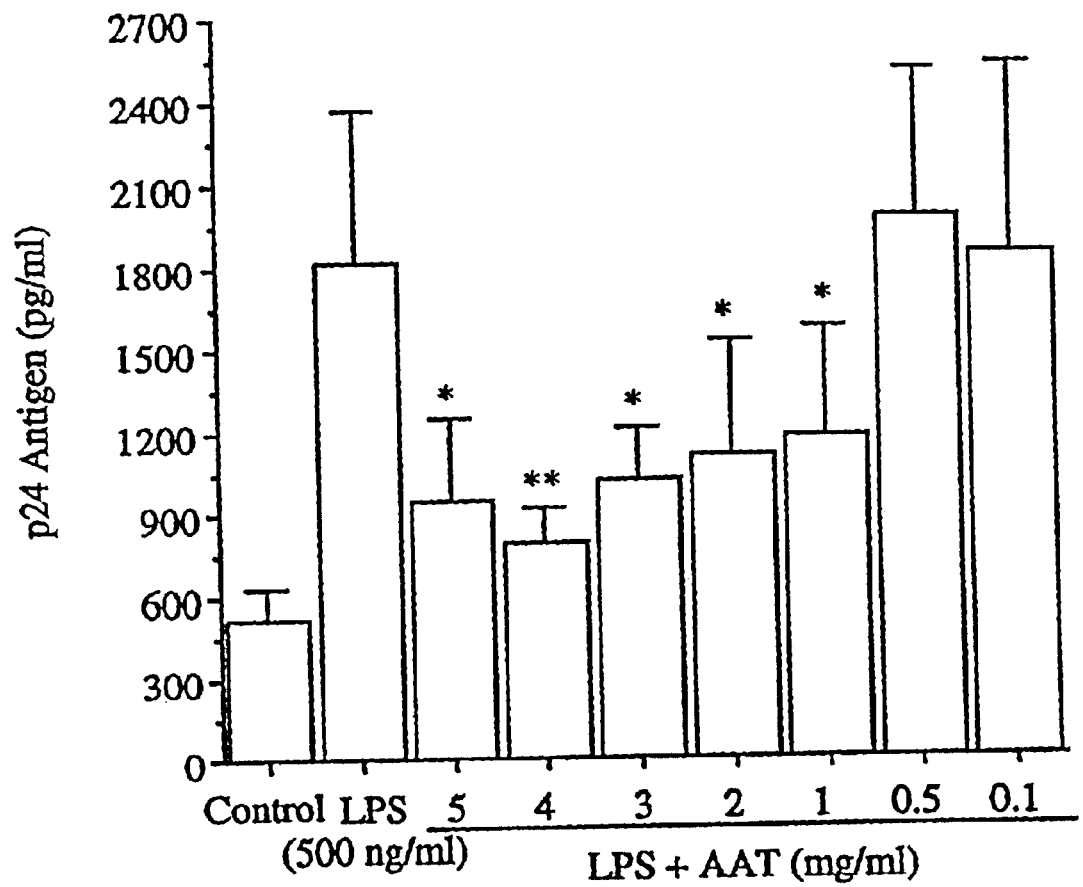
FIG. 9 illustrates the effect of AAT on HIV production in U1 cells upon induction with LPS.

LPS is a cell wall component of gram-negative bacteria with several pro-inflammatory activities. In 3 experiments, U1 cells cultured in the presence of 500 ng/ml LPS for 48 hrs contained 1,427±39 pg/ml p24 antigen, as shown in FIG. 9. This represents a mean 3-fold increase compared to p24 produced in control (medium alone) cultures, where 476±76 pg/ml p24 antigen was measured. U1 cells stimulated with LPS in the presence of 0.1, 0.5, 1, 2, 3, 4, and 5 mg/ml AAT contained 1,531, ±436,1,543, ±427, 1,108±241, 913±287, 782, ±187, 578, ±155, 626±257, pg/ml p24 antigen, respectively. Addition of AAT at 3, 4, and 5 mg/ml inhibited p24 production by 71, 90 and 86%, respectively.

AAT Inhibits NaCl-Induced HIV-1 in U1 Cell Cultures.

Figure 10:
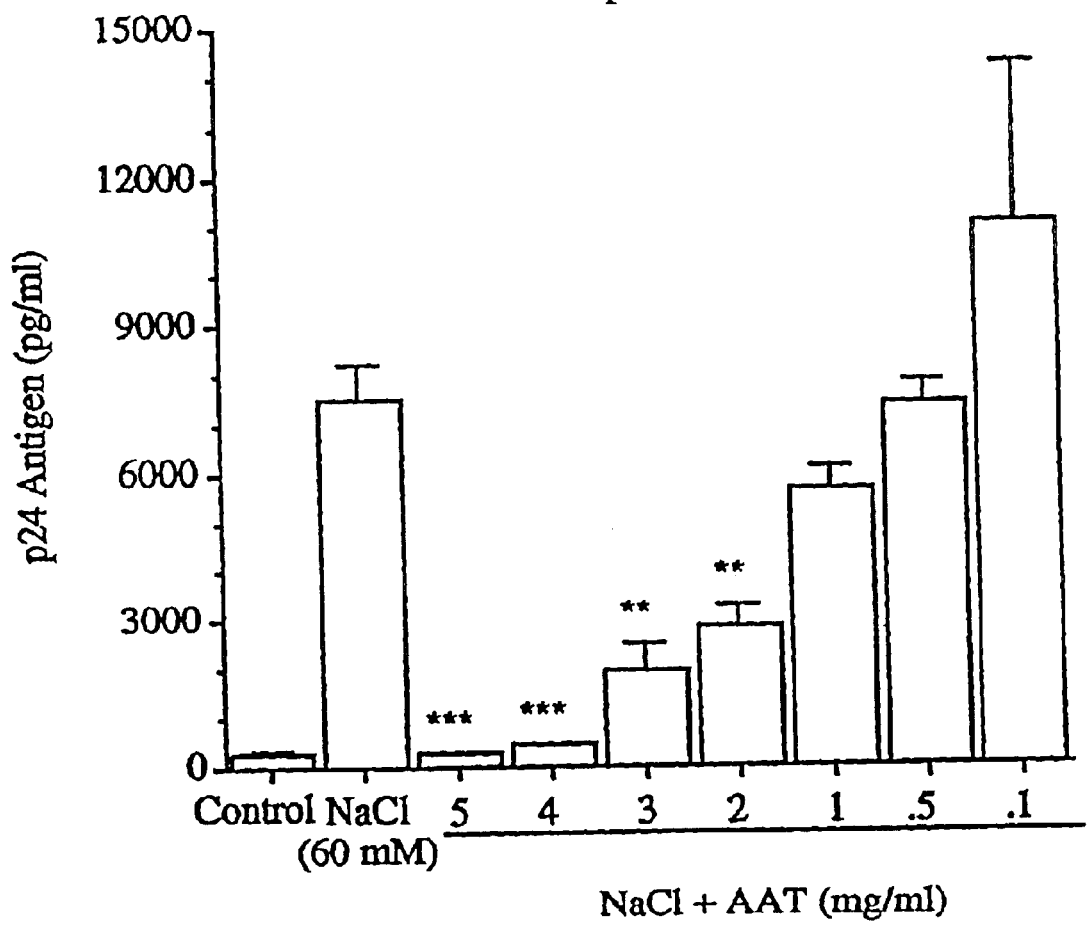
FIG. 10 illustrates the effect of AAT on HIV production in U1 cells upon induction with NaCl.

To exclude the possibility that AAT-induced inhibition of cytokine-stimulated p24 is due to protein—protein interactions, hyperosmolarity is used as the p24-inducing stimulus. Previous studies have established 60 mM NaCl as a potent inducer of p24 antigen in U1 cell cultures. The effect of AAT on NaCl-induced p24 in 3 experiments is tested and the results are shown in FIG. 10. A large (26-fold) increase in mean p24 antigen production in cultures is observed in the presence of NaCl alone as compared to control (medium alone) cultures. The mean p24 antigen measured in NaCl-stimulated and control cultures are 7,511±707 and 295±29 pg/ml, respectively. Stimulation with 60 mM NaCl in the presence of 0.1, 0.5, 1.0, 2.0, 3.0, 4.0 and 5.0 mg/ml AAT resulted in mean p24 levels of 11,054±3, 231, 7,363±485, 5,657±48, 2,83 8±466, 1,919±594, 425±32 and 266±26 pg/ml, respectively. For AAT added at 3.0, 4.0 and 5.0 mg/mL the corresponding percent inhibitions are 76,98.3 and 100% (FIG. 10).

AAT Inhibits p24 Antigen Production in HIV-1-Infected PBMC.

Figure 2:
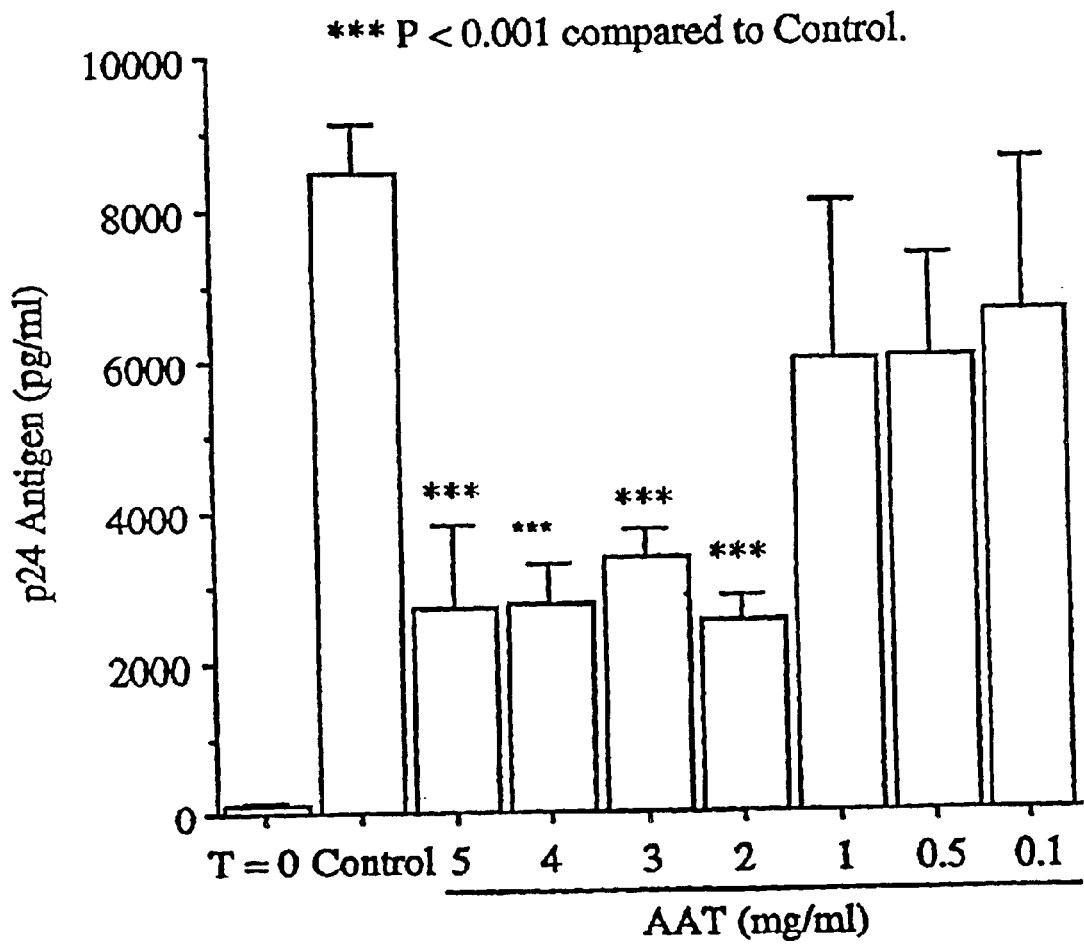
FIG. 2 illustrates the effect of AAT on HIV production in PBMC as performed with pre-incubation.

The effect of AAT on freshly-infected PBMC is tested to assess activity in a primary cell model of HIV-1 infection. PBMC isolated from 3 healthy volunteers are infected with lymphocyte-tropic HIV-1 as described above. FIGS. 1 and 2 show results obtained for PBMC infected with HIV-1 in the absence or presence of 3 mg/ml AAT at the time of infection. A large increase in p24 antigen occurred over the 4 days of culture, with 180±63 pg/ml p24 measured at time t=0 and 7,781±1,650 pg/ml p24 measured after 4 days (R3 medium alone, control). This represents a mean 43-fold increase in p24 (P<0.001). Under these conditions, PBMC cultured for 4 days with AAT added at 0.1, 0.5, 1.0, 2.0, 3.0, 4.0 and 5.0 mg/ml produced 8,687±1,304, 7,392±1,299, 6,613, 6,258±1, 772, 5,275±316, 4,725±101, and 3,508 pg/ml p24, respectively. Compared to control cultures, significant reductions in p24 antigen are observed for added AAT concentrations of 4.0 and 5.0 mg/ml (22 and 46% reductions, respectively).

As shown in (b), compared to time 0 a significant increase in p24 production is observed in control cultures after 4 days of culture, with values of 107±52 and 8,478±629 pg/ml, respectively (mean 79-fold increase, P<0.001). PBMC cultured in the presence of AAT added at 0.1, 0.5, 1.0, 2.0, 3.0, 4.0 and 5.0 mg/ml produced 6,620±2,026, 6,047±1,322, 6,014±2,055, 2,516±345, 3,360±371, 2,743±316 and 2,713±645 pg/ml, respectively. Significant reductions in p24 antigen in cultures exposed to AAT compared to control cultures are observed for AAT concentrations of 2.0, 3.0, 4.0 and 5.0 mg/ml AAT. Compared to control cultures, these AAT concentrations resulted in reductions in p24 production of 71, 61, 65 and 67%, respectively.

AAT Inhibits Early Infection-Associated Events in MAGI-CCR5 Cells Exposed to HIV-1.

Figure 3:
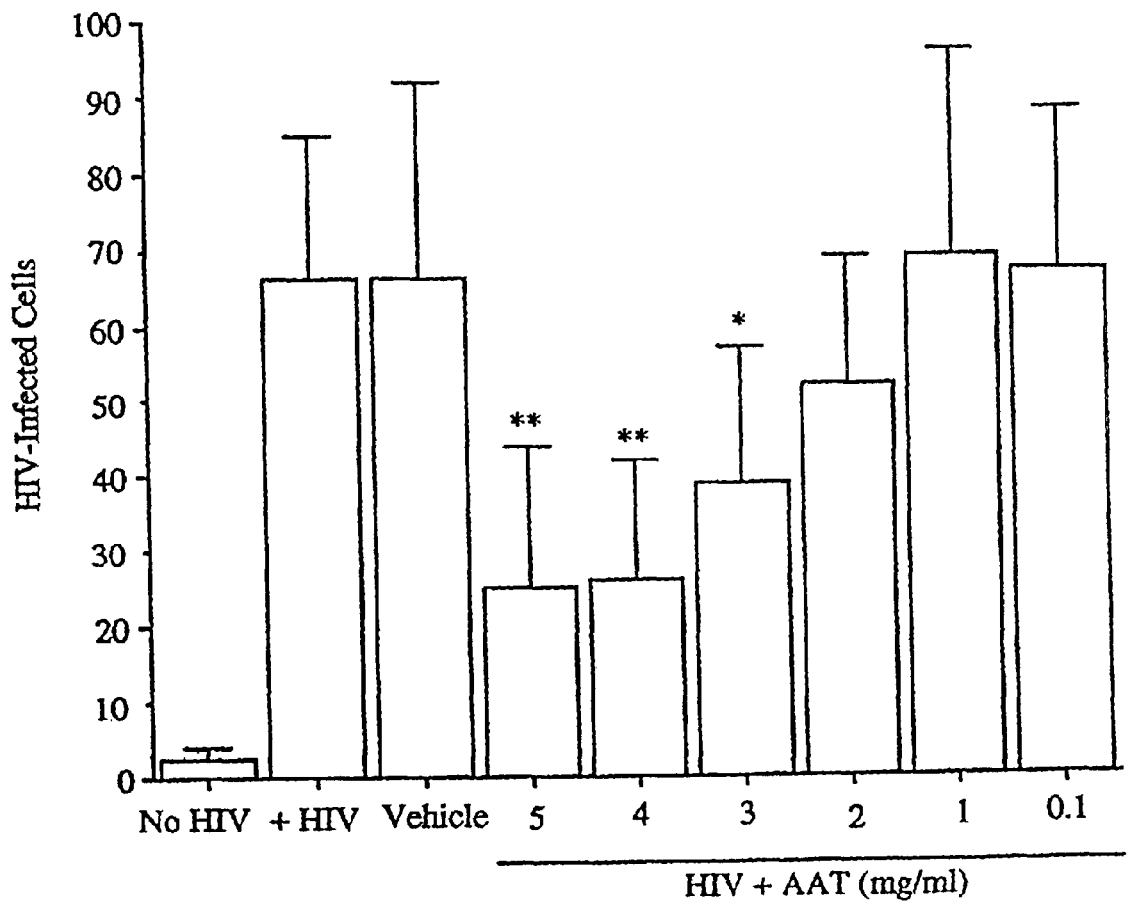
FIG. 3 illustrates the effect of AAT on HIV production in MAGI cells.

The MAGI-CCR-5 cell assay evaluates early events in the HIV-1 infection process. These events include cell-surface binding and internalization, uncoating, reverse transcription and translation, protein processing and Tat activity. Binding of the tat protein to a reporter construct within the MAGI-CCR-5 cells enables quantification of these early HIV-1 events. In 3 separate experiments shown in FIGS. 3 and 4, MAGI-CCR-5 cells are infected with A018A strain of HIV-1 as described supra. In cultures conducted in the absence of virus (no HIV-1), a mean positive cell count of 2.3 is obtained. In the presence of HIV-1 (+HIV-1 ), an increase in mean positive cell count is observed, to 72±13 (31-fold increase, P<0.001). MAGI-CCR-5 cells exposed to HIV-1 and cultured with added AAT demonstrate significant and dose-dependent inhibition of positive cell counts. Addition of 0.1, 1.0, 2.0, 3.0, 4.0 and 5.0 mg/ml AAT resulted in mean positive cell counts of 74±13, 75±17, 56±II, 45±12, 28±9, and 21±12, respectively.

Compared to cultures containing HIV-1 alone, significant inhibition of MAGI-CCR-5 cell early infection events is significant for AAT concentrations of 2.0, 3.0, 4.0 and 5.0 mg/ml. These values correspond to 23, 41, 66 and 76% inhibition. As a vehicle control, MAGI-CCR-5 cells are exposed to virus and a diluent volume equivalent to that of AAT solution added to 5.0 mg/ml cultures. Cultures containing diluent produced a positive cell count of 72±16, which is not significantly different from cultures containing HIV-1 alone (+HIV), as shown on the horizontal axis.

Example 3

Failure of Commercial AAT Preparation (Prolastin) to Inhibit HIV

Figure 6:
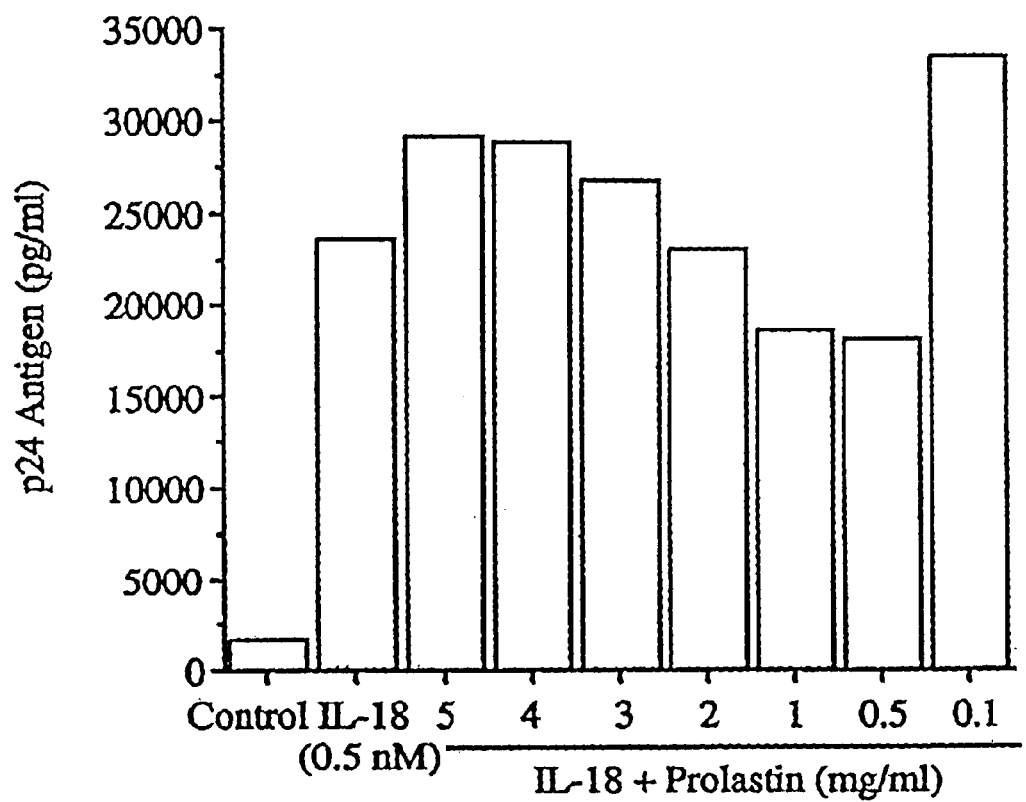
FIG. 6 illustrates the lack of effect of Prolastin on HIV production in U1 cells upon induction with IL-18.

Prolastin used as a control preparation of AAT in the experimental setting that is similar to those described above. Surprisingly, this preparation fails to display anti-HIV activity at doses that are comparable to the composition of the invention (FIG. 6). The lack of the activity cannot be explained by low levels of active AAT since Prolastin contains only about 8% of inactive form of total antitrypsin (Lomas D A, Elliott P R, Carrell R W. Commercial plasma alpha1-antitrypsin (Prolastin) contains a conformationally inactive, latent component. Eur Respir J 1997 March; 10(3):672–5). The biological significance of this observation is unknown. However, this means that not every AAT composition is inherently antivirally active, which may explain why prior to this invention others failed to discover the anti-HIV activity of AAT. Upon this unexpected observation a series of tests are carried out to further investigate the significance lm of AAT and its role as naturally occurring anti-HIV substance. Whole blood collected from at least 12 healthy donors and containing relatively normal levels of functionally active AAT is resistant to HIV infection. As can be seen from FIG. 13, in healthy individuals HIV p24 antigen levels on day 4 postinfection (T=4d) are not significantly higher than at inoculation (T=0) (shown in FIG. 13 as two bars on the left). In contrast, blood from AAT-deficient humans is highly susceptible to HIV infection. FIG. 13 shows that lack of functional AAT makes cells from such individuals prone to HIV infection.

Example 4

Effect of Select Peptides on HIV

Figure 4:
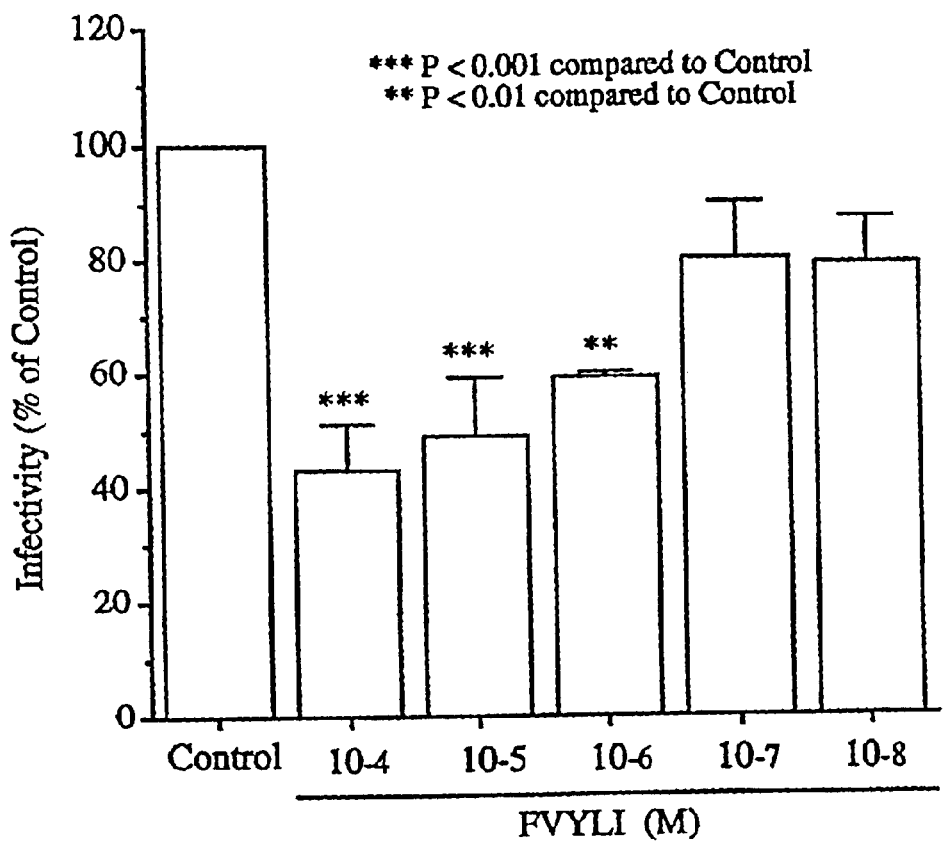
FIG. 4 illustrates the effect of FVYLI (SEQUENCE ID NO. 16) peptide on HIV production in MAGI cells.
Figure 5:
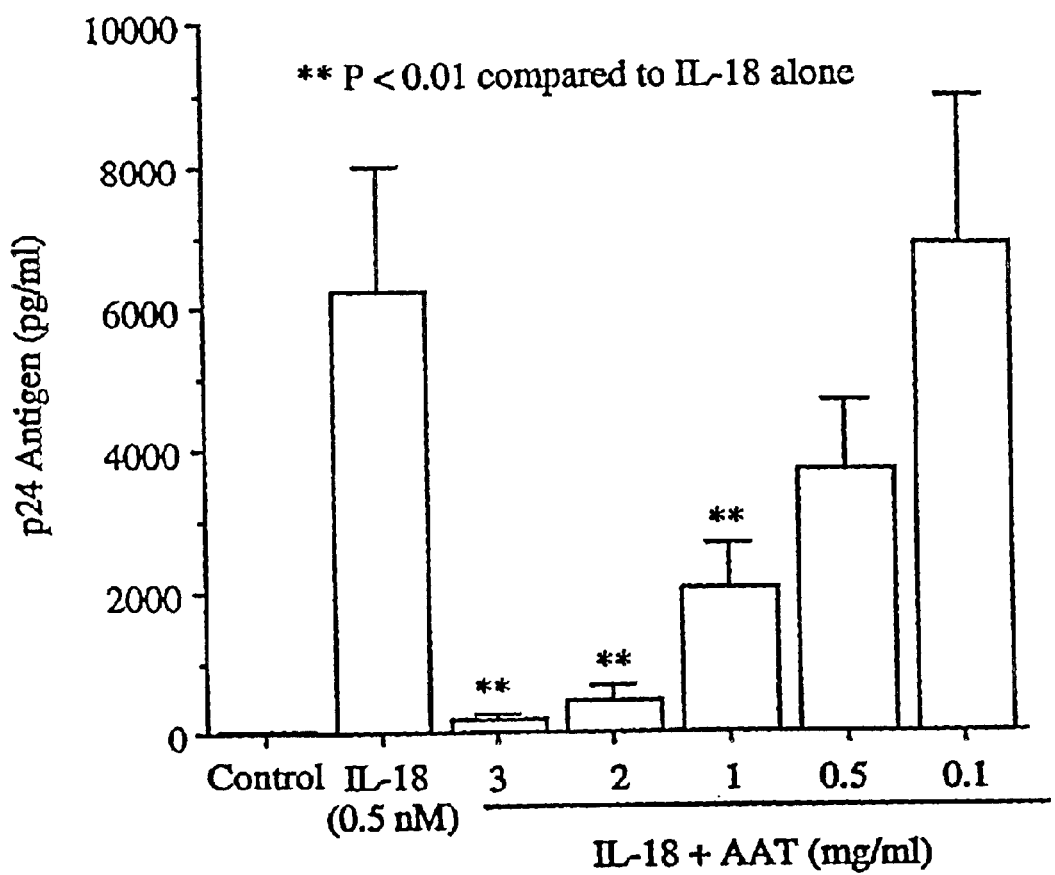
FIG. 5 illustrates the effect of AAT on HIV production in U1 cells upon induction with IL-18.

FIG. 4 shows representative results obtained with a carboxyterminal peptide FVYLI (SEQUENCE ID NO. 16) that is derived but not necessarily identical to a respective C-terminal pentapeptide from AAT. Other short peptides such as FVFLM (SEQUENCE ID NO. 1), FVFAM (SEQUENCE ID NO. 2), FVALM (SEQUENCE ID NO. 3), FVFLA (SEQUENCE ID NO. 4), FLVFI (SEQUENCE ID NO. 5), FLMII (SEQUENCE ID NO. 6), FLFVL (SEQUENCE ID NO. 7), FLFVV (SEQUENCE ID NO. 8), FLFLI (SEQUENCED NO. 9), FLFFI (SEQUENCE ID NO. 10), FLMFI (SEQUENCE ID NO. 11), FMLLI (SEQUENCE ID NO. 12), FIIMI (SEQUENCE ID NO. 13), FLFCI (SEQUENCE ID NO. 14), FLFAV (SEQUENCE ID NO. 15), FVYLI (SEQUENCE ID NO. 16), FAFLM (SEQUENCE ID NO. 17), AVFLM (SEQUENCE ID NO. 18) demonstrate more or less similar effect (not shown). They are active at approximately similar molar range when used alone or in combination, when mixtures thereof are added to the MAGI cultures. It is concluded that peptides derived from or homologous and/or analogous to this particular C-terminal region of AAT are equally antivirally active as a whole AAT molecule. This observation is totally unexpected since peptide fragments of such size are not anticipated to replace large size AAT molecule.

Example 5

Anti-HIV Effect of Drugs Having AAT Activity

Figure 11:
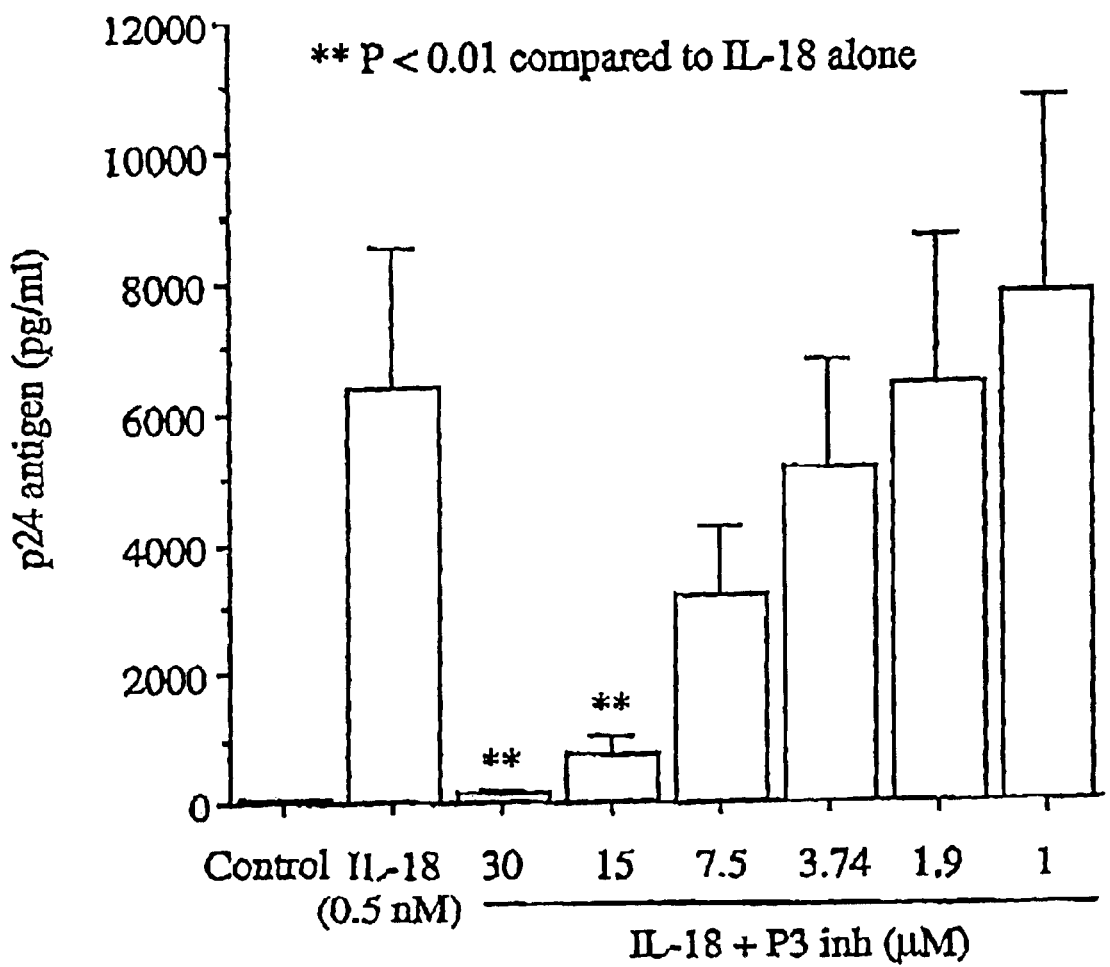
FIG. 11 illustrates the effect of AAT-mimicking drug on HIV production in U1 cells upon induction with IL-18.
Figure 12:
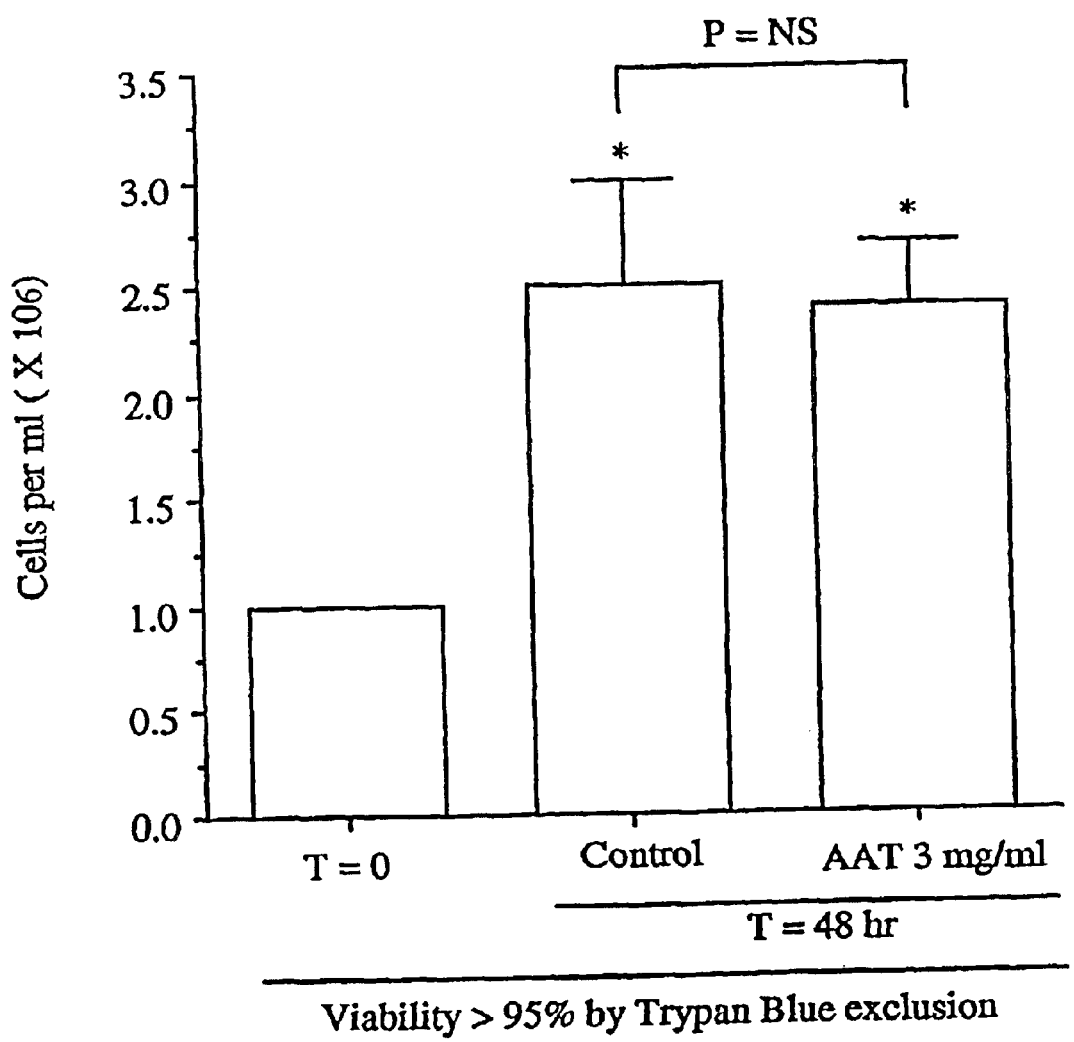
FIG. 12 illustrates the effect of AAT on viability and number of U1 cells.

A series of drugs that may mimic AAT activity are tested for anti-HIV activity. These man-made drugs are made according to methods described in WO 98/24806, which discloses substituted oxadiazole, thiadiazole and triazole as serine protease inhibitors. In addition, U.S. Pat. No. 5,874,585 discloses substituted heterocyclic compounds useful as inhibitors of serine proteases; U.S. Pat. No. 5,869,455 discloses N-substituted derivatives; U.S. Pat. No. 5,861,380 discloses protease inhibitors-keto and di-keto containing ring systems; U.S. Pat. No. 5,807,829 discloses serine protease inhibitor-tripeptoid analogues; U.S. Pat. No. 5,801,148 discloses serine protease inhibitors-proline analogues; U.S. Pat. No. 5,618,792 discloses substituted heterocyclic compounds useful as inhibitors of serine proteases. Surprisingly, several of these drugs demonstrate anti-HIV activity at micromolar ranges. As a representative example shown in FIG. 11, a synthetic molecule (protease 3 inhibitor or P3 inh) mimicking AAT displays significant anti-HIV effect in the same experimental condition as in Example 1.

As used hereinafter P3 inh is also designated as CE-2072 or (Benzyloxycarbonyl)-L-valyl-N-[1-(2-(3-methylbenzyl)-1,3,4-oxadiazolyl]carbonyl)-2-(S)-methylpropyl]-L-prolinamide. Methods of preparing P3 inh and derivatives thereof are disclosed in detail in U.S. Pat. No. 5,807,829 and incorporated by way of reference. CE 2072 along with AAT is tested in an assay that demonstrates the effect of these substances on NF-KB expression, which is induced by IL-18. Lane 4 in FIG. 13 shows band that corresponds to IL-18-induced NF-KB which is much larger than NF-KB in controls (lane 1) not stimulated by IL-18. In the presence of either AAT (lane 7) or AAT-mimicking synthetic molecule (lane 10) the NF-κB expression is reduced, indicating that these substances down-regulate NF-κB expression. This is a totally unexpected observation as these serine protease inhibitors are not known to interfere with NF-KB expression.

Example 7

Antiviral Activity of Man-Made Small Molecules

Without limiting to AAT and peptide derivatives of AAT, the compounds like oxadiazole, thiadiazole and triazole peptoids are preferred as they also show an equivalent antiviral activity in a mouse model as described in above Example 3. Anti-HIV effective doses are in a range from about 1 $\mu$g/kg to approximately 100 mg/kg. Specific examples of such oxadiazole, thiadiazole and triazole peptoids are molecules such as Benzyloxycarbonyl-L-valyl-N-[1-(2-(3-methylbenzyl)-1,3,4-oxadiazolyl]carbonyl)-2-(S)-methylpropyl]-L-prolinamide; Benzyloxycarbonyl-L-valyl-N-[1-(2-(5-(methyl)-1,3,4-oxadiazoly]carbonyl-2-(S)-methylpropyl]-L-prolinamide; Benzyloxycarbonyl)-L-valyl-N-[1-(2-(5-(3-trifluoromethylbenzoyl)-1,3,4-oxadiazolyl]carbonyl)-2-(S)-methylpropyl]-L-prolinamide Benzyloxycarbonyl)-L-valyl-N-[1-(2-(5-(4-Dimethylaminobenzyl)-1,3,4-oxadiazolyl]carbonyl)-2-(S)-methylpropyl]-L-prolinamide; Benzyloxycarbonyl)-L-valyl-N-[1-(2-(5-(1-napthylenyl)-1,3,4-oxadiazolyl]carbonyl)-2-(S)-methylpropyl]-L-prolinamide; (Benzyloxycarbonyl)-L-valyl-[1-(3(5-(3,4-methylenedioxybenzyl)-1,2,4-oxadiazolyl]carbonyl)-2-(S) methylpropyl]-L-prolinamide; Benzyloxycarbonyl)-L-valyl-N-[1-(3-(5-(3,5-dimethylbenzyl)-1,2,4-oxadiazolyl] carbonyl)-2-(S)-methylpropyl]-L-prolinamide; (Benzyloxycarbonyl)-L-valyl-N-[1-(3-(5-(3,5-dimethoxybenzyl)-1,2,4-oxadiazolyl]carbonyl)-2-(S)-methylpropyl]-Lprolinamide; (Benzyloxycarbonyl)-L-valyl-N-[1-(3-(5-(3,5-ditrifluoromethylbenzyl)-1,2,4-oxadiazolyl]carbonyl)-2-(S)-methylpropyl]-L prolinamide; (Benzyloxycarbonyl)-L-valyl-N-[1-(3-(5-(3-methylbenzyl)-1,2,4-oxadiazolyl]carbonyl)-2-(S)-methylpropyl]-Lprolinamide; (Benzyloxycarbonyl)-L-valyl-N-[1-(3-(5-(biphenylmethine)-1,2,4-oxadiazolyl]carbonyl)-2-(S)-methylpropyl]-L-prolinamide; (Benzyloxycarbonyl)-L-valyl-N-[1-(3-(5-(4-phenylbenzyl) 1,2,4-oxadiazolyl] carbonyl)-2-(S)-methylpropyl]-L-prolinamide; (Benzyloxycarbonyl)-L-valyl-N-[1-(3-(5-(3-phenylbenzyl)-1,2,4-oxadiazolyl]carbonyl)-2-(S)-methylpropyl]-Lprolinamide; (Benzyloxycarbonyl)-L-valyl-N-[1-(3-(5-(3-phenoxybenzyl)-1,2,4-oxadiazolyl]carbonyl)-2-(S)-methylpropyl]-Lprolinamide; (Benzyloxycarbonyl)-L-valyl-N-[1-(3-(5-(cyclohexylmethylene)-1,2,4-oxadiazolyl] carbonyl)-2-(S)-methylpropyl]-L-prolinamide; (Benzyloxycarbonyl)-L-valyl-N-[1-(3-(5-(3-trifluoromethyldimethylmethylene)-1,2,4-oxadiazolyl] carbonyl)-2-(S)-methylpropyl]-L, prolinamide;

(Benzyloxycarbonyl)-L-valyl-N-[1-(3-(5-(1-napthylmethylene)-1,2,4-, oxadiazolyl]carbonyl)-2-(S)-methylpropyl]-L-prolinamide; (Benzyloxycarbonyl)-L-valyl-N-[1-(3-(5-(3-pyridylmethyl)-1,2,4-oxadiazolyl]carbonyl)-2-(S)-methylpropyl]-L-prolinamide; (Benzyloxycarbonyl)-L-valyl-N-[1-(3-(5-(3,5-diphenylbenzyl) 1,2,4-oxadiazolyl]carbonyl)-2-(S)methylpropyl]-L-prolinamide; (Benzyloxycarbonyl)-L-valyl-N-[1-(3-(5-(4-dimethylaminobenzyl)-1,2,4-oxadiazolyl]carbonyl)-2-(S)-methylpropyl]-L-prolinamide; 2-(5-[(Benzyloxycarbonyl)amino]-6-oxo-2-(4-fluorophenyl)- 1,6-dihydro-1-pyrimidinyl]-N-(1-(3-(5-(3-trifluoromethylbenzoyl)-1,2,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-2-(S) methylpropyl]acetamide; 2-(5-[(Benzyloxycarbonyl) amino]-6-oxo-2-(4-fluorophenyl)-1,6-dihydro-1-pyrimidinyl]-N-[1-(2-(5-(3-methylbenzyl)-1,3,4-oxadiazolyl]carbonyl)-(S)-2-methylpropyl]acetamide; 2-(5-Amino-6oxo-2-(4-fluorophenyl)-1,6-dihydro-1-pyrimidinyl 3-N-[1-(2-(5-(3-methylbenzyl)-1,3,4 oxadiazolyl] carbonyl)-2-methylpropyl] acetamide; (Pyrrole-2-carbonyl)-N-(benzyl)glycyl-N-[1-(2-(5-(3-methylbenzyl)-1,3,4-oxadiazolyl]carbonyl)-2-(S)-methylpropyl)amide; (Pyrrole-2-carbonyl)-N-(benzyl)glycyl-N-(1-(3-(5-(3-trifluoromethylbenzyl)]-1,2,4-oxadiazolyl)-(S)-methylpropyl]amide; (2S, 5S)-5-Amino-1,2,4,5,6,7-hexahydroazepino-[3,2, 1]-indole-4one-carbonyl-N-[1-(2-(5-(3-methylbenzyl)-1,3,4-oxadiazolyl]carbonyl)-(R,S)-2-methylpropyl]amide; BTD-[ ]-(2-(5-(3-methylbenzyl)-1,3,4-oxadiazolyl]carbonyl)-2-(S)-methylpropyl]amide; (R,S)-3-Amino-2oxo-5-phenyl-1,4-benzodiazepine-N-[1-(2-(5-(3-methylbenzyl)-1,3,4-oxadiazolyl]carbonyl)-2-(S)-methylpropyl]acetamide; (Benzyloxycarbonyl)-L-valyl-2-(2,3-dihydro-1H-indole)-N-[1-(2-(5-(3-methylbenzyl)-1,3,4-oxadiazolyl]carbonyl)-2-(S)-methylpropyl]amide; (Benzyloxycarbonyl)-L-valyl-2-L-(2,3-dihydro-1H-indole)-N-[1-(3-(5-(3-trifluoromethylbenzyl)-1,2,4-oxadiazolyl]carbonyl)-2-(S)-methylpropyl]amide; Acetyl-2-L-(2,3-dihydro-1H-indole)-N-[1-(2-(5-(3-methylbenzyl)-1,3,4-oxadiazolyl]carbonyl)-2-(S)-methylpropyl]amide; 3-(S)-(Benzyloxycarbonyl)amino)-epsilon-lactam-N-[1-(2-(5-(3methylbenzy 1)-1,3,4-oxadiazolyl]carbonyl)-2-(S)-methylpropyl acetamide; 3-(S)-(Amino)-epsilon-lactam-N-[1-(2-(5-(3-methylbenzyl)-1,3,4-oxadiazolyl]carbonyl)-2-(S)-methylpropyl]acetamide trifluoroacetic acid salt; 3-(S)-[(4-morpholinocarbonyl-butanoyl)amino]-epsilon-lactam-N-[1-(2-(5-(3-methylbenzyl)-1,3,4-oxadiazolyl]carbonyl)-2-(R,S)-methylpropyl]acetamide; 6-[4-Fluorophenyl]-epsilon-lactam-N-[1-(2-(5-(3-methylbenzyl)-1,3,4-oxadiazolyl]carbonyl)-2-(S)-methylpropyl]acetamide; 2-(2-(R,S)-Phenyl-4-oxothiazolidin-3-yl]-N-[1-(2-(5-(3-methylbenzyl)-1,3,4-oxadiazolyl]carbonyl)-2-(S)-methylpropyl]acetamide; 2-(2-(R,S)-phenyl-4-oxothiazolidin-3-y]-N-[1-(2-(5-(3-methylbenzyl)-1,3,4-oxadiazolyl]hydroxymethyl)-2-(S)-methylpropyl] acetamide; 2-(2R,S)-Benzyl-4-oxothiazolidin-3-yl]-N-[1-(2-(5-(3-methylbenzyl)-1,3,4-oxadiazolyl]carbonyl)-2-(S)-methylpropyl]-acetamide; 2-(2-(R,S)-Benzyl-4-oxothiazolidin-3-yloxide]-N-[1-(3-(5-(3-trifluoromethylbenzyl)-1,2,4-oxadiazolyl]carbonyl)-2-(R, S)-methylpropyl]acetamide; (1-Benzoyl-3,8-quinazolinedione)-N-[1-(2-(5-(3-methylbenzyl)-1 ,3,4-oxadiazolyl]carbonyl)-2-(S)-methylpropyl]acetamide; (1Benzoyl-3,6-piperazinedione)-N-[1-(2-(5-(3-methylbenzyl)-1,3,4-oxadiazolyl]carbonyl)-2-(S)-methylpropyl]acetamide; (1-Phenyl-3,6-piperazinedione)-N-[1-(2-(5-(3-methylbenzyl)-1,3,4-oxadiazolyl]carbonyl)-2-(S)-methylpropyl]acetamide; [(1-Phenyl-3,6-piperazinedione)-N-[1-(3-(5-(3-trifluoromethylbenzyl)-1,2, 4-oxadiazolyl]carbonyl)]-2-(S)-methylpropyl]acetamide; 3-[(Benzyloxycarbonyl) amino]-quinolin-2-one-N-[1-(2-(5-(3-methylbenzyl)-1,3,4-oxadiazolyl]carbonyl)-2-(S)-methylpropyl]acetamide; 3-[(Benzyloxycarbonyl)amino]-7-piperidinyl-quinolin-2-one-N-1-(2-(5-(3-methylbenzyl)-1,3, 4-oxadiazolyl]carbonyl)-2-(S)-methylpropyl]acetamide; 3-(Carbomethoxy-quinolin-2-one-N-[1-(2-(5-(3-methybenzyl)-1,3,4-oxadiazolyl]carbonyl)-2-(S)-methylpropyl]acetamide; 3-(Amino-quinolin-2-one)-N-t 1-(2-(5-(3-methylbenzyl)-1,3,4-oxadiazolyl]carbonyl)-2-(S)-methylpropyl]acetamide; 3-[(4-Morpholino)aceto] amino-quinolin-2-one-N-[1-(2-(5-(3-methylbenzyl)-1,3,4-oxadiazolyl]carbonyl)-2-(S)-methylpropyl]acetamide; 3,4-Dihydro-quinolin-2-one-N-[1-(2-(5-(3-methylbenzyl)-1,3, 4-oxadiazolyl]carbonyl)-2-(S)-methylpropyl]acetamide; 1-Acetyl-3-(4-fluorobenzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-dimethylaminobenzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-carbomethoxybenzylidene)piperazine-2,5-dione-N-f 1-(2-(5-(3-methylbenzyl)-1,3,4-oxadiazolyl]carbonyl)-2-(S)-methylpropyl]acetamide; 1-Acetyl-3-[(4-pyridyl) methylene]piperazine-2,5-dione-N-f 1-(2-(5-(3-methylbenzyl)-1,3,4-oxadiazolyl]carbonyl)-2-(S)-methylpropyl]acetamide; 4-[1-Benzyl-3-(R)-benzyl-piperazine-2,5-dione]-N-[1-(2-[5-(3-methylbenzyl)-1,3, 4oxadiazolyl]carbonyl)-2-(S)-methylpropyl]acetamide; 4-[1-Benzyl-3-(S)-benzyl piperazine-2,5-dione]-N-[1-(2-(5-(3-methylbenzyl)-1,3,4-oxadiazoly]carbonyl)-2-(S)-methylpropyl]acetamide; 4-[1-Benzyl-3(R)-benzylpiperazine-2,5-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzyl piperazine-2,5,-dione]-N-[1-(3-(5-(2-dimethylaminoethyl)-1,2,4-oxadiazolyl]carbonyl)-2-(S)-methylpropyl]acetamide; 4-[1-Methyl-3-(R,S)-phenylpiperazine-2,5,-dione]-N-[1-(3-(5-(3-trifluoromethylbenzyl)-1,2,4-oxadiazolyl]carbonyl)-2-(S)-methylpropyl]acetamide; 4-[[-Methyl-3-(R,S)-phenylpiperazine-2,5,-dione)]-N-[1-(2-(5-(3-methylbenzyl)-1,3,4-oxadiazolyl]carbonyl)-2-(S)-methylpropyl]acetamide; 4-[1-(4-Morpholinoethyl)3-(R)-benzylpiperazine-2,5,-dione]-N-[1-(2-(5-(3-methylbenzyl)-1,3,4-oxadiazolyl]carbonyl)-2-(S)-methylpropyl]acetamide; 5-(R,S)-Phenyl-2,4-imidazolidinedione-N-[1-(2-(5-(3-methylbenzyl)-1,3,4-oxadiazolyl]carbonyl)-2-(S)-methylpropyl]acetamide; 5-(R)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(3-(5-(3-trifluoromethylbenzyl))-1, 2,4-oxadiazolyl]carbonyl)-2-(S)-methylpropyl]acetamide; 5-(R)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 1-Benzyl-4-(R)-benzyl-2,5-imidazolidinedione-N-[1-(2-(5-(3-methylbenzyl)-1,3,4-oxadiazolyl]carbonyl)-2-(S)-methylpropyl]acetamide; and 1-Benzyl(R)-benzyl-2,5-imidazolidinedione-N-[1-(3-(5-(3-trifluoromethylbenzyl)-1,2,4-oxadiazolyl]carbonyl)-2-(S)-methylpropyl]acetamide among others. Methods of making these molecules and derivatives thereof are well known in the art and can be found for example in U.S. Pat. Nos. 5,807,829; 5,891,852; 5,869,455; 5,861,380; and 5,801,148, which is incorporated herein by way of reference in its entirety.

Other small man-made molecules useful in this invention comprise phenylenedialkanoate esters, which are also effective in the mouse model. Specific examples of certain phenylenedialkanoate esters include but are not limited to: 2,2'-(1,4-phenylene)dibutyric acid; tert-butyl-3-chloro-pivaloate; dimethyl-2,2'-(1,4-phenylene)diisobutyrate; 2,2'-(1,4-phenylene)diisobutyric acid; bis(sulfoxides); Obis(sulfones); and bis(4-(2'-carboxy-2'-methylpropylsulfonyl)phenyl)2,2'-(1,4-phenylene)diisobutyrate among others. More specifically, U.S. Pat. No. 5,216,022 teaches other small molecules useful for the practice of this invention, including: Benzyloxycarbonyl-L-valyl-N-[1-(2-[5-(3-methylbenzyl)-1,3,4-oxadiazolyl]carbonyl)-2-(S)-methylpropyl]-L-prolinamide (also known as CE-2072), Benzyloxycarbonyl-L-valyl-N-[1-(2-(3-methylbenzyl)-1,3,4-oxadiazolyl]carbonyl)-2-(S)-methylpropyl]-L-prolinamide; Benzyloxycarbonyl-L-valyl-N-[1-(2-(5-(methyl)-1,3,4-oxadiazoly]carbonyl)-2-(S)-methylpropyl]-L-prolinamide; Benzyloxycarbonyl)-L-valyl-N-[1-(2-(5-(3-trifluoromethylbenzyl)-1,3,4-oxadiazolyl]carbonyl)-2-(S)-methylpropyl]-L-prolinamide; (Benzyloxycarbonyl)-L-valyl-N-[1-(2-(5-(4-Dimethylaminobenzyl)-1,3,4-oxadiazolyl]carbonyl)-2-(S)-methylpropyl]-L prolinamide; Benzyloxycarbonyl)-L-valyl-N-[1-(2-(5-(1-napthylenyl)-1,3,4-oxadiazolyl]carbonyl)-2-(S)-methylpropyl]-L-prolinamide; (Benzyloxycarbonyl)-L-valyl-[1-(3-(5-(3,4-methylenedioxybenzyl)-1,2,4-oxadiazolyl]carbonyl)-2-(S)-methylpropyl]-Lprolinamide; Benzyloxycarbonyl)-L-valyl-N-(1-(3-(5-(3,5-dimethylbenzyl)-1,2,4-oxadiazolyl]carbonyl)-2-(S)-methylpropyl]-L-prolinamide; (Benzyloxycarbonyl)-L-valyl-N-[1-(3-(5-(3,5-dimethoxybenzyl)-1,2,4-oxadiazolyl]carbonyl)-2-(S)-methylpropyl]-Lprolinamide; (Benzyloxycarbonyl)-L-valyl-N-[1-(3-(5-(3,5-ditrifluoromethylbenzyl)-1,2,4-oxadiazolyl]carbonyl)-2-(S)-methylpropyl]-L-prolinamide; (Benzyloxycarbonyl)-L-valyl-N-[1-(3-(5-(3-methylbenzyl)-1,2,4oxadiazolyl]carbonyl)-2-(S)-methylpropyl]-Lprolinamide; (Benzyloxycarbonyl)-L-valyl-N–1(3-(5-(biphenylmethine)-1,2,4-oxadiazolyl]carbonyl)-2-(S)-methylpropyl]-L-prolinamide; (Benzyloxycarbonyl)-L-valyl-N-1-(3-(5-(4-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenoxybenzyl)-1,2,4-oxadiazolyl]carbonyl)-2-(S)-methylpropyl]-L-prolinamide; (Benzyloxycarbonyl)-L-valyl-N-[1-(3-(5-(cyclohexylmethylene)-1,2,4-oxadiazolyl]carbonyl)-2-(S)-methylpropyl]-L-prolinamide; (Benzyloxycarbonyl)-L-valyl-N-[1-(3-(5-(3-trifluoromethyldimethylmethylene)-1,2,4-oxadiazolyl]carbonyl)-2-(S)-methylpropyl]-L prolinamide; (Benzyloxycarbonyl)-L-valyl-N-[1-(3-(5-(1-napthylmethylene)-1,2,4-oxadiazolyl]carbonyl)-2-(S)-methylpropyl]-L-prolinamide; (Benzyloxycarbonyl)-L-valyl-N-[1-(3-(5-(3-pyridylmethyl)-1,2,4-oxadiazolyl]carbonyl)-2-(S)-methylpropyl]-Lprolinamide; (Benzyloxycarbonyl)-L-valyl-N-[1-(3-(5-(3,5-diphenylbenzyl)-1,2,4-oxadiazolyl]carbonyl)-2-(S)-methylpropyl]-Lprolinamide; (Benzyloxycarbonyl)-L-valyl-N-(1-(3-(5-(4-dimethylaminobenzyl)-1,2,4-oxadiazolyl]carbonyl)-2-(S)-methylpropyl]-L-prolinamide; 2-(5-[(Benzyloxycarbonyl)amino]-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-2-(S)-methylpropyl]acetamide; 2-(5-[(Benzyloxycarbonyl)amino]-6-oxo-2-(4-fluorophenyl)-1,6-dihydro-1-pyrimidinyl]-N-[1-(2-(5-(3-methylbenzyl)-1,3,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1 (2-(5-(3-methylbenzyl)-1,3,4oxadiazolyl]carbonyl)-2-methylpropyl]acetamide; (Pyrrole-2-carbonyl)-N-(benzyl)glycyl-N-[1-L) (2-(S-(3-methylbenzyl)-1,3,4-oxadiazolyl]carbonyl)-2-(S)-methylpropyl]amide; (Pyrrole-2carbonyl)-N-(benzyl)glycyl-N-[1-(3-(5-(3-trifluoromethylbenzyl)]-1,2,4-oxadiazolyl)-(S)-methylpropyl]amide; (2,5S)(5S)-5-Amino-1,2,4,5,6,7-hexahydroazepino-[3,2, 1]-indole-4-one-carbonyl-N-[1-(2-(5-(3-methylbenzyl)-1,3,4-oxadiazolyl]carbonyl)-(R,S)-2-methylpropyl]amide; BTD-[1-(2-(5-(3-methylbenzyl)-1,3,4-oxadiazolyl]carbonyl)-2-(S)-methylpropyl]amide; g,S)-3-Amino-2-oxo-5-phenyl-1,4,-benzodiazepine-N-[1-(2-(5-(3-methylbenzyl)-]-2,3,4-oxadiazolyl]carbonyl)-2-(S)-methylpropyl]acetamide; (Benzyloxycarbonyl)-L-valyl-2-L-(2,3-dihydro-1H-indole)-N-[1-(2-(5-(3-methylbenzyl)-1,3,4-oxadiazolyl]carbonyl)-2-(S)-methylpropyl]amide; (Benzyloxycarbonyl)-L-valyl-2-L-(2,3-dihydro-1H-indole)-N-f 1-(3-(5-(3-trifluoromethylbenzyl)-1,2,4-oxadiazolyl)carbonyl)-2-(S)-methylpropyl]amide; Acetyl-2-L-(2,3-dihydro-1H-indole)-N-[1-(2-(5-(3-methylbenzyl)-1,3,4-oxadiazolyl]carbonyl)-2-(S)-methylpropyl]amide; 3-(S)-(Benzyloxycarbonyl)amino)-c-lactam-N-[1-(2-(5-(3-methylbenzyl)-1,3,4-oxadiazolyl]carbonyl)-2-(S)-methylpropyl]acetamide; 3-(S)-(Amino)-ϵ-lactam-N-[1-(2-(5-(3-methylbenzyl)-1,3, 4-oxadiazolyl]carbonyl)-2-(S)-methylpropyl]acetamide trifluoroacetic acid salt; 3-(S)-[(4-morpholinocarbonyl-butanoyl)amino]-ϵ-lactam-N-[1-(2-(5-(3-methylbenzyl)-1, 3,4-oxadiazolyl]carbonyl)-2-(R,S)-methylpropyl] acetamide; 6-[4-Fluorophenyl]-ϵ-lactam-N-[1-(2-(5-(3-methylbenzyl)-1,3,4-oxadiazolyl]carbonyl)-2-(S)-methylpropyl]acetamide; 2-(2-(R,S)-Phenyl-4-oxothiazolidin-3-yl]-N-[1-(2-(5-(3-methylbenzyl)-1,3,4-oxadiazolyl]carbonyl)-2-(S)-methylpropyl]acetamide; 2-(2-(R,S)-phenyl-4-oxothiazolidin-3-yl]-N-[1-(2-(5-(3-methylbenzyl)-1,3,4-oxadiazolyl]hydroxymethyl)-2-(S)-methylpropyl]acetamide; 2-(2-(R,S)-Benzyl-4-oxothiazolidin-3-yl]-N-[1-(2-(5-(3-methylbenzyl)-1,3,4-oxadiazolyl]carbonyl)-2-(S)-methylpropyl]-acetamide; 2-(2-(R,S)-Benzyl-4-oxothiazolidin-3-yl oxide]-N-[1-(3-(5-(3-trifluoromethylbenzyl)-1,2,4-oxadiazolyl]carbonyl)-2-(R,S,)-methylpropyl]acetamide; (1-Benzoyl-3,8-quinazolinedione)-N-[1-(2-(5-(3-methylbenzyl)-1,3,4-oxadiazolyl]carbonyl)-2-(S)-methylpropyl]acetamide; (1-Benzoyl-3,6-piperazinedione)-N-[1-(2-(5-(3-methylbenzyl)-1,3,4-oxadiazolyl]carbonyl)-2-(S)-methylpropyl]acetamide; (1-Phenyl-3,6piperazinedione)-N-1-(2-(5-(3-methylbenzyl)-1,3,4-oxadiazolyl)-2-(S)-methylpropyl]acetamide; [(1-Phenyl-3,6-piperazinedione)-N-f 1-(3-(5-(3-trifluoromethylbenzyl)-1,2, 4-oxadiazolyl)carbonyl)]-2-(S)-methylpropyl]acetamide; 3-[(Benzyloxycarbonyl)amino]-quinolin-2-one-N-[1-(2-(5-(3-methylbenzyl)-1,3,4-oxadiazolyl]carbonyl)-2-(S)- methylpropyl]acetamide; 3-[(Benzyloxycarbonyl)amino]-7-piperidinyl-quinolin-2-one-N-[1-(2-(5-(3-methylbenzyl)-1,3,4-oxadiazolyl]carbonyl)-2-(S)-methylpropyl]acetamide; 3-(Carbomethoxy-quinolin-2-one-N-[1-(2-(5-(3-methybenzyl)-1,3,4-oxadiazolyl]carbonyl)-2-(S)-methylpropyl]acetamide; 3-(Amino-quinolin-2-one)-N-[1-(2-(5-(3-methylbenzyl)-1,3,4-oxadiazolyl]carbonyl)-2-(S)-methylpropyl]acetamide; 3-[(4-Morpholino)aceto]amino-quinolin-2-one-N-[1-(2-(5-(3-methylbenzyl)-1,3,4-oxadiazolyl]carbonyl)-2-(S)-methylpropyl]acetamide; 3,4-Dihydro-quinolin-2-one-N-[1-(2-(5-(3-methylbenzyl)-1,3,4-oxadiazolyl]carbonyl)-2S)-methylpropyl]acetamide; 1-Acetyl-3-(4-fluorobenzylidene) piperazine-2,5-dione-N-[1-(2-(5-(3-methylbenzyl)-1,3,4-oxadiazolyl]carbonyl)-2-(S)-methylpropyl]acetamide; 1-Acetyl-3-(4-dimethylaminobenzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-carbomethoxybenzylidene)piperazine-2,5-dione-N-[1-(2-(5-(3-methylbenzyl) 1,3,4-oxadiazolyl)carbonyl)-2-(S)-methylpropyl]acetamide; 1-Acetyl-3-[(4pyridyl)methylene] piperazine-2,5-dione-N-[1-(2-(5-(3-methylbenzyl)-1,3,4-oxadiazolyl]carbonyl)-2-(S)-methylpropyl]acetamide; 4-[1-Benzyl-3-(R)-benzyl-piperazine-2,5,-dione]-N-[1-(2-[5-(3-methylbenzyl)-1,3,4-oxadiazolyl]carbonyl)-2-(S)-methylpropyl]acetamide; 4-[1-Benzyl-3-(S)-benzyl piperazine-2,5,-dione]-N-[1-(2-(5-(3-methylbenzyl)-1,3,4-oxadiazolyl]carbonyl)-2-(S)-methylpropyl]acetamide; 4-f 1-Benzyl-3(R)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzyl piperazine-2,5,-dione)-N-[1-(3-(5-(2-dimethylaminoethyl)-1,2,4-oxadiazolyl]carbonyl)-2-(S)-methylpropyl]acetamide; 4-[1-Methyl-3-(R,S)-phenylpiperazine-2,5,-dione]-N-[1-(3-(5-(3-trifluoromethylbenzyl)-1,2,4-oxadiazolyl]carbonyl)-2-(S)-methylpropyl]acetamide; 4-[[-Methyl-3-(R,S)-phenylpiperazine-2,5,-dione]-N-[1-(2-(5-(3-methylbenzyl)-1,3,4-oxadiazolyl]carbonyl)-2-(S)-methylpropyl]acetamide; 4-[1-(4-Morpholinoethyl)3-(R)-benzylpiperazine-2,5,-dione]-N-[1-(2-(5-(3-methylbenzyl)-1,3,4-oxadiazolyl] carbonyl)-2-(S)-methylpropyl]acetamide; 5-(R,S)-Phenyl-2,4-imidazolidinedione-N-[1-(2-(5-(3-methylbenzyl)-1,3,4-oxadiazolyl]carbonyl)-2S)-methylpropyl]acetamide; 5-(R)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 5-(R)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 1-Benzyl-4-(R)-benzyl-2,5-imidazolidinedione-N-[1-(2-(5-(3-methylbenzyl)-1,3,4-oxadiazolyl]carbonyl)-2-(S)-methylpropyl]acetamide; and 1-Benzyl-4-(R)-benzyl-2,5-imidazolidinedione-N-[1-(3-(5-(3-trifluoromethylbenzyl)-1,2,4-oxadiazolyl]carbonyl)-2-(S)-methylpropyl]acetamide among others. Methods of making these molecules and derivatives thereof are well known in the art and can be found in aforementioned U.S. Pat. No. 5,216,022, which is incorporated herein by way of reference in its entirety.

Likewise, U.S. Pat. No. 5,869,455 discloses N-substituted derivatives; U.S. Pat. No. 5,861,380 protease inhibitors-keto and di-keto containing ring systems; U.S. Pat. No. 5,807,829 serine protease inhibitor—tripeptoid analogues; U.S. Pat. No. 5,801,148 serine protease inhibitors-proline analogues; U.S. Pat. No. 5,618,792 substituted heterocyclic compounds useful as inhibitors of serine proteases. These patents and PCT publications and others as listed infra are enclosed herein by reference. Other equally advantageous molecules, which may be used instead of $\alpha_1$-antitrypsin or in combination with $\alpha_1$-antitrypsin are contemplated such as in WO 98/20034 disclosing serine protease inhibitors from fleas. Without limiting to this single reference one skilled in the art can easily and without undue experimentation adopt compounds such as in WO98123565 which discloses aminoguanidine and alkoxyguanidine compounds useful for inhibiting serine proteases; WO98/50342 discloses bis-aminomethylcarbonyl compounds useful for treating cysteine and serine protease disorders; WO98/50420 cyclic and other amino acid derivatives useful for thrombin-related diseases; WO 97/21690 D-amino acid containing derivatives; WO 97/10231 ketomethylene group containing inhibitors of serine and cysteine proteases; WO 97/03679 phosphorous containing inhibitors of serine and cysteine proteases; WO 98/21186 benzothiazo and related heterocyclic inhibitors of serine proteases; WO 98/22619 discloses a combination of inhibitors binding to P site of serine proteases with chelating site of divalent cations; WO 98/22098 a composition which inhibits conversion of pro-enzyme CPP32 subfamily including caspase 3 (CPP32/Yama/Apopain); WO 97/48706 pyrrolo-pyrazine-diones; WO 97133996 human placental bikunin (recombinant) as serine protease inhibitor; WO 98/46597 complex amino acid containing molecule for treating viral infections and conditions disclosed hereinabove.

Other compounds having serine protease inhibitory activity are equally suitable and effective including but not limited to tetrazole derivatives as disclosed in WO 97/24339; guanidinobenzoic acid derivatives as disclosed in WO 97/37969 and in a number of U.S. Pat. Nos. 4,283,418; 4,843,094; 4,310,533; 4,283,418; 4,224,342; 4,021,472; 5,376,655; 5,247,084; and 5,077,428; phenylsulfonylamide derivatives represented by general formula in WO 97/45402; novel sulfide, sulfoxide and sulfone derivatives represented by general formula in WO 97/49679; novel amidino derivatives represented by general formula in WO 99/41231; other amidinophenol derivatives as disclosed in U.S. Pat. Nos. 5,432,178; 5,622,984; 5,614,555; 5,514,713; 5,110,602; 5,004,612; and 4,889,723 among many others.

In summary, the Examples recited hereinabove show that compounds exhibiting AAT activity such as AAT, peptides derived analogous or homologous to C-terminal end of AAT, and man-made synthetic molecules mimicking AAT action, display herpes virus-suppressive effects in vitro and in vivo.

Example 7

Synergy of AAT and AAT-Related Molecules With Anti-HIV Drugs

AAT and AAT-related molecules displaying AAT activity are tested for possible utility as a combination therapy with established anti-HIV drugs. Among these compositions are nucleoside reverse transcriptase (RT) inhibitors such as Retrovir (AZT/zidovudine; Glaxo Wellcome); Epivir (3TC, lamivudine; Glaxo Wellcome); Videx (ddI/didanosine; Bristol-Myers Squibb); Hivid (ddC/zalcitabine; Hoffmann-La Roche); Zerit (d4T/stavudine; Bristol-Myers Squibb); Ziagen (abacavir, 1592U89; Glaxo Wellcome); Hydrea (Hydroxyurea/HO; Bristol-Myers Squibb) and non-nucleoside reverse transcriptase inhibitors (NNRTIs) such as Viramune (nevirapine; Roxane Laboratories); Rescriptor (delavirdine; Pharmacia & Upjohn); Sustiva (efavirenz, DMP-266; DuPont Merck); Preveon (adefovir dipivoxil, bis-POM PMEA; Gilead). Also tested are aspartyl protease inhibitors (PI's) including Fortovase (saquinavir; Hoffmann-La Roche); Norvir (ritonavir, Abbott Laboratories); Crixivan (indinavir; Merck & Company); Viracept (nelfinavir, Agouron Pharmaceuticals); and Angenerase (amprenavir/1141W94; Glaxo Wellcome). The presence of the compositions of the present invention enhances the antiviral effect of above-listed drugs.

In summary, the studies presented supra demonstrate HIV-1-suppressive activity of AAT and related compounds with AAT activity in all three in vitro models; U1 cells, PBMC, and MAGI cells. To anyone skilled in the art it is obvious that these models closely relate to the in vivo situation. This is further supported by the commercial and clinical success of existing, publicly available anti-HIV drugs (listed in Example 6) which were all initially tested in similar in vitro models. The results from such models are highly and invariably predictable of the success or failure in clinical setting. Experiments conducted in U1 cells establish the blockade of HIV-1 production in a chronic infection model. This inhibitory effect is observed for all stimuli tested, including inflammatory cytokines (IL-18, IL-6, TNF) LPS and hyperosmolarity. The inhibitory effect is potent, with a range of inhibition of 73–100%. Since AAT is not known to have intracellular antiprotease activity (size of AAT molecule is too large to cross the plasma membrane), these results suggest the existence of an extracellular protease(s) required for virion production. Although pro-inflammatory cytokines and LPS are not known to physically interact with AAT, we excluded this mechanism of AAT inhibition by hyperosmolarity-induced HIV-1. Hyperosmolarity established by adding NaCl to U1 cell cultures increased p24 antigen production. As shown in FIG. 10, 60 mM NaCl added to culture resulted in a 26-fold increase in p24 concentration compared to control. This increase is completely inhibited in the presence of 5 mg/ml AAT.

Results obtained in HIV-1-infected PBMC demonstrate several characteristics of AAT inhibition. Experiments are performed in PBMC from three donors infected in the absence or presence of AAT during infection. The presence of AAT during infection did not affect p24 antigen production following removal of AAT and 4 days of culture in medium alone. Therefore, any effects of AAT at the time of infection are reversible. However, AAT effects during the infection period are established by the enhancement of AAT effect when added to PBMC following infection and cultured for 4 days. Enhancement of 4 day AAT effect is manifested by a larger maximal suppression and by suppression at lower AAT concentrations. Maximal p24 reductions in PBMC exposed to AAT for 4 days are 46% and 71% for cells infected in the absence or presence of AAT, respectively. For cells infected in the absence of AAT, a significant suppressive effect is observed for post-infection AAT added at 5 and 4 mg/ml, and for cells infected in the presence of AAT significant effect is obtained at 5, 4, 3, and 2 mg/ml. Considered together, these data indicate a reversible enhancing effect of AAT when present at the time of PBMC infection.

Experiments performed in MAGI-CCR-5 cells (FIGS. 3 and 4) indicate inhibitory effects of AAT and related compounds on early infection-associated events. The observed dose-dependent effect is maximal at 5 mg/ml AAT, where 76% inhibition is observed compared to control (HIV-1 added in the absence of AAT). Therefore, AAT inhibits HIV-1 events prior to integration into the host-cell genome (cell-surface receptor binding, internalization, integration, uncoating, reverse transcription, translation and protein processing and (at activation).

Also, AAT, peptides derived analogous or homologous to C-terminal end of AAT, and 1 representative man-made synthetic molecules mimicking AAT action, display HIV-1-suppressive effects operative during both early (PBMC and MAGI-CCR-5 cell results) and late (U1 cell results) events associated with HIV-1 infection. Unexpectedly, the synergy appears to exist between known AIDS drugs belonging to RT and PI classes and compositions of this invention, which belong to unrelated class of inhibitors, i.e., serpins.

Throughout this application various publications and patents are referenced. The disclosures of these publications and patents in their entireties are hereby incorporated by reference into this application in order to more fully describe the state of the art to which this invention pertains.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for inhibiting human immunodeficiency virus (HIV) replication in a patient harboring said HIV comprising administering to the patient a combination comprising:
   at least one first compound exhibiting α1-antitrypsin (AAT)-like protease inhibiting activiity, wherein said compound exhibiting AAT-like proteaase inhibiting activity is a
   i. (benzyloxycarbonyl)-L-valyl-N-[1-(3-(5-(3-trifluoromethylbenzyl)-1,2,4-oxadiazolyl)carbonyl)-2-(S)-methylpropyl]-L-prolinamide;
   ii. (benzyloxycarbonyl)-L-valyl-N-[1-(3-(5-(2-phenylethyl)-1,2,4-oxadiazolyl)carbonyl)-2-(S)-methylpropyl]-L-prolinamide;
   iii. (benzyloxycarbonyl)-L-valyl-N-[1-(3-(5-(2-methoxybenzyl)-1,2,4-oxadiazolyl)carbonyl)-2-(S)-methylpropyl]-L-prolinamide:
   iv. (benzyloxycarbonyl)-L-valyl-N-[1-(3-(5-(trifluoromethyl)-1,2,4-oxadiazolyl)carbonyl)-2-(S)-methylpropyl]-L-prolinamide;
   v. (benzyloxycarbonyl)-L-valyl-N-[1-(3-(5-(methyl)-1 2,4-oxadiazolyl)carbonyl)-2S)-methylpropyl]-L-prolinamide;
   vi. (benzyloxycarbonyl)-L-valyl-N-1-(3-(5-(difluoromethyl)-1,2,4-oxadiazolyl)carbonyl)-2-(S)-methylpropyl]-L-prolinamide;
   vii. (benzyloxycarbonyl)-L-valyl-N-[1-(3-(-5-(1benzyl)-1,2,4-oxadiazolyl)carbonyl)-2-(S)-methylpropyl]-L-prolinamide;
   viii. (benzyloxycarbonyl)-L-valyl-N-[1-(3-(5-(3-methoxybenzyl)-1,2,4-oxadiazolyl)carbonyl)-2-(S)-methylpropyl]-L-prolinamide:
   ix. (benzyloxycarbonyl)-L-valyl-N-[-(3-(5-(2,6-difluorobenzyl)-1,2,4-oxadiazolyl)carbonyl)-2-(S)-methylpropyl-L-prolinamide,
   x. (benzyloxycarbonyl)-L-valyl-N-[1-(3-(5-(trans-styryl-1,2,4-oxadiazolyl)carbonyl)-2-(S)-methylpropyl]-L-prolinamide,
   xi. (benzyloxycarbonyl)-L-valyl-N-[1-(3-(5-(trans-4-trifluoromethylstryryl)-1,2,4-oxadiazolyl)carbonyl)-2-(S)-methylpropyl]-L-prolinamide:
   xii. (benzyloxycarbonyl)-L-valyl-N-[1-(3-(5-(trans-4-methoxystyryl)-1,2,4-oxadiazolyl)carbonyl)-24S)-methylpropyl]-L-prolinamide:
   xiii. (benzyloxycarbonyl)-L-valyl-N-[1-(3-(5-(3-thienylmethyl)-1,2,4-oxadiazolyl)carbonyl)-2-(S)-methylpropyl]-L-prolinamide
   xiv. (benzyloxycarbonyl)-L-valyl-N-[1-(3-(5-(phenyl)-1,2,4-oxadiazolyl)carbonyl)-2-(S)-methylpropyl]-L-prolinamide;
   xv. (benzyloxycarbonyl)-L-valyl-N-[1-(3-(5(-3-phenylpropyl)-1,2,4-oxadiazolyl)carbonyl)-2-(S)-methylpropyl]-L-prolinamide.
   xvi. (benzyloxycarbonyl)-L-valyl-N-[1-(2-(3-(methylbenzyl)-1-(3-oxadiazolyl)carbonyl)-2-(S)-methylpropyl]-L-prolinamide,
   xvii. (benzyloxycarbonyl)-L-valyl-N-[1-(2-(5-(methyl)-1,3,4-oxadiazolyl)carbohyl)-2-(S)-methylpropyl]-L-prolinamide,
   xviii. (benzyloxycarbonyl)-L-valyl-N-[1-(2-(5-(3-trifluoromethylbenzyl)-1,3,4-oxadiazolyl)carbonyl)-2-(S)-methylpropyl]-L-prolinamide:
   xix. (benzyloxycarbonyl)-L-valyl-N-[1-(2-(5-(4-dimethylamino benzyl)-1,3,4-oxadiazolyl)carbonyl)-2-(S)-methylpropyl]-L-prolinamide:

xx. (benzyloxycarbonyl)-L-valyl-N-[1-(2-(5-(1-napthylenyl)-1,3,4-oxadiazolyl)carbonyl)-2-(S)-methylpropyl]-L-prolinamide:

xxi. (benzyloxycarbonyl)-L-valyl-[1-(3-(5-(3,4-methylenedioxybenzyl)-1,2,4-oxadiazolyl)carbonyl)-2-(S)-methylpropyl]-L-prolinamide:

xxii. (benzyloxycarbonyl)-L-valyl-N-[1-(3-(5-(3,5-dimethylbenzyl)-1,2,4-oxadiazolyl)carbonyl)-2-(S)-methylpropyl]-L-prolinamide;

xxiii. (benzyloxycarbonyl)-L-valyl-N-[1-(3-(5-(3,5-dimethoxybenzyl)-1,2,4-oxadiazolyl)carbonyl)-2-(S)-methylpropyl]-L-prolinamide:

xxiv. (benzyloxycarbonyl)-L-valyl-N-[1-(3-(5-(3-5-ditrifluoromethylbenzyl)-1,2,4-oxadiazolyl)carbonyl)-2-(S)-methylpropyl]-L-prolinamide, xxv. (benzyloxycarbonyl)L-valyl-N-[1-(3-(5-(3-methylbenzyl)-1,2,4-oxadiazolyl)carbonyl)-2-(S)-methylpropyl]-L-prolinamide:

xxvi. (benzyloxycarbonyl)-L-valyl-N-[1-(3-(5-(biphenylmethine)-1,2,4-oxadiazolyl)carbonyl)-2-(S)-methylpropyl]-L-Prolinamide;

xxvii. (benzyloxycarbonyl)-L-valyl-N-[1-(3-(5-(4-phenylbenzyl)-1,2,4-oxadiazolyl]carbonyl)-2-(S)-methylpropyl]-L-prolinamide;

xxiii. (benzyloxycarbonyl)-L-valyl-N-[1-(3-(5-(3-phenylbenzyl)-1,2,4-oxadiazolyl)carbonyl)-2-(S)-methylpropyl]-L-prolinamide;

xxix. (benzyloxycarbonyl)-L-valyl-N-[1-(3-(5-(3-phenoxybenzyl)-1,2,4-oxadiazolyl)carbonyl) -2-(S)-methylpropyl]-L-prolinamide:

xxx. (benzyloxycarbonyl)-L-valyl-N-[1-(3-(5-(cyclohexylmethylene)-1,2.4 oxadiazolyl)carbonyl)-2-(S)-methylpropyl]-L-prolinamide;

xxxi. (benzyloxycarbonyl)-L-valyl-N-[1-(3-(5-(3-trifluoromethyldimethylmethylene) 1,2,4-oxadiazolyl)carbonyl)-2-(S)-methylpropyl]-L-prolinamide;

xxxii. (benzyloxycarbonyl)-L-valyl-N-[1-(3-(5-(1-napthylmethylene)-1,2,4-oxadiazolyl)carbonyl)-2-(S)-methylpropyl]-L-prolinamide;

xxxiii. (benzyloxycarbonyl)-L-valyl-N-[1-(3-(5-(3-pyridylmethyl)-1,2,4-oxadiazolyl)carbonyl)-2-(S)-methylpropyl]-L-prolinamide;

xxxiv. (benzoxycarbonyl)-L-valyl-N-[1-(3-(5-(3,5-diphenylbenzyl)-1,2,4-oxadiazolyl)carbonyl)-2-(S)-methylpropyl]-L-prolinamide;

xxxv. (benzyloxycarbonyl)-L-valyl-N-[1-(3-(5-(4-dimethylaminobenzyl)-1,2,4-oxadiazolyl)carbonyl)-2-(S)-methylpropyl]-L-prolinamide;

xxxvi. 2-(5-[(benzyloxycarbonyl)amino]-6-oxo-2-(4-fluorophenyl)-1,6-dihydro-1-pyrimidinyl-N-[1-(3-(5-(3-trifluoromethylbenzyl)-1,2,4-oxadiazolyl)carbonyl)-(S)-2-methylpropyl]acetamide;

xxxvii. 2-(5-amino-6-oxo-2-(4-fluorophenyl)-1,6-dihydro-1-pyrimidinyl]-N-[1-(3-(5-(3-trifluoromethylbenzyl)-1,2,4-oxadiazolyl)carbonyl)-2-(S)-methylpropyl]acetamide;

xxxviii. 2-(5-[(benzyloxycarbonyl)amino]-6-oxo-2-(4-fluorophenyl)-10.6-dihydro-1-pyrimidinyl]-N-f 1-(2-(5-(3-methylbenzyl)-1,3,4-oxadiazolyl)carbonyl)-(S)-2-methylpropyl]acetamide;

xxxix. 2-[5-amino-6-oxo-2-(4-fluorophenyl)-1,6-dihydro-1-pyrimidinyl]-N-[1-(2-(5-(3-methylbenzyl)-1,3,4-oxadiazolyl)carbonyl)-2-methylpropyl]acetamide;

xl. (pyrrole-2-carbonyl)-N-(benzyl)glycyl-N-[1-(245-(3-methylbenzyl)-1,3,4-oxadiazolyl)carbonyl)-2-(S)-methylpropyl]amide;

xli. (pyrrole-2-carbonyl)-N-(benzyl)glycyl-N-[1-(3-(5-(3-trifluoromethylbenzyl)(1,2,4-oxadiazolyl)-(S)-methylpropyl]amide;

xlii. (2S, 5S)-5-amino-1,2,4,5,6,7-hexahydroazepino-[3,2,1-indole-4-one-carbonyl-N-[2-(5-(3-methylbenzyl)-1,3,4-oxadiazolyl)carbonyl)-(R,S)-2-methylpropyl]amide;

xliii. BTD-[1-(2-(5-(3-methylbenzyl)-1,3,4-oxadiazolyl)carbonyl)-2-(S)-methylpropyl]amide;

xliv. (R,S)-3-amino-2-oxo-5-phenyl-1,4-benzodiazepine-N-[1-(2-(5-(3-methylbenzyl)-1,3,4-oxadiazolyl)carbonyl)-2-(S)-methylpropyl]acetamide;

xlv. (benzyloxycarbonyl)-L-valyl-2-L-(2,3-dihydro-1H-indole)-N-[1-(2-(5-(3-methylbenzyl)-1,3,4-oxadiazolyl)carbonyl)-2-(S)-methylpropyl]amide;

xlvi. (benzyloxycarbonyl)-L-valyl-2-L-(2,3-dihydro-1H-indole)-N-[1-(3-(5-(3-trifluoromethylbenzyl)-1,2,4-oxadiazolyl)carbonyl)-2-(S)-methylpropyl]amide;

xlvii. acetyl-2-L-(2,3-dihydro-1H-indole)-N-[1-(2-(5-(3-methylbenzyl)-1,3,4-oxadiazolyl)carbonyl)-2-(S)-methylpropyl]amide;

xlviii. 3-(S)-(benzyloxycarbonyl)amino)-e-lactam-N-[1-(2-(5-(3-methylbenzyl)-1,3,4-oxadiazolyl)carbonyl)-2-(S)-methylpropyl]acetamide;

xlix. 3-(S)-(amino)-e-lactam-N-[1-2-(5-(3-methylbenzyl)-1,3,4-oxadiazolyl)carbonyl)-2-(S)-methylpropyl]acetamide trifluoroacetic acid salt;

1,3-(S)-[(4-morpholinocarbonyl-butanoyl)amino]-e-lactam-N-[1-(2-(5-(3-methylbenzyl)-1,3,4-oxadiazolyl)carbonyl)-2-(R,S)-methyl propyl]acetamide;

li. 6-[4-fluorophenyl]-e-lactam-N-[1-(2-(5-(3-methylbenzyl)-1,3,4-oxadiazolyl)carbonyl)-2-(S)-methylpropyl]acetamide;

lii. 2-(2-(R,S)-phenyl-4-oxothiazolidin-3-yl]-N-[1-(2-(5-(3-methylbenzyl)-1,3,4-oxadiazolyl)carbonyl)-2-(S)-methylpropyl]acetamide;

liii. 2-(2-(R,S)-phenyl-4-oxothiazolidin-3-yl]-N-[1-(2-(5-(3-methylbenzyl)-1,3,4-oxadiazolyl(hydroxymethyl)-2-(S)-methylpropyl]acetamide;

liv. 2-(2-(R,S)-benzyl-4-oxothiazolidin-3-yl]-N-1-(2-(5-(3-methylbenzyl)-1,3,4 oxadiazolyl)carbonyl)-2-(S)-methylpropyl]acetamide;

lv. 2-(2-(R,S)-benzyl-4-oxothiazolidin-3-yl oxide]-N-[1-(3-(5-(3-trifluoromethylbenzyl)-1,2,4-oxadiazolyl)carbonyl)-2-(R,S,)-methylpropyl]acetamide;

lvi. (1-benzoyl-3,8-quinazolinedione)-N-[1 1-(2-(5-(3-methylbenzyl)-1,3,4-oxadiazolyl)carbonyl)-2-(S)-methylpropyl]acetamide;

lvii. (1-benzoyl-3.6-piperazinedione)-N-[1-(2-(5-(3-methylbenzyl)-1,3,4-oxadiazolyl)carbonyl)-2-(S)-methylpropyl]acetamide;

lvii. (1-phenyl-3,6-piperazinedione)-N-[1-(2-(5-(3-methylbenzyl)-1,3,4-oxadiazolyl)carbonyl)-2-(S)-methylpropyl]acetamide;

lix. (1-phenyl-3,6-piperazinedione)-N-[1-(3-(5-(3-trifluoromethylbenzyl)-1,2,4-oxadiazolyl)carbonyl)-2-(S)-methylpropyl]acetamide;

lx. 3-[(benzyloxycarbonyl)amino]-quinolin-2-one-N-[1-(2(5-(3-methylbenzyl)-1,3,4-oxadiazolyl)carbonyl)]-2-(S)-methylpropyl]acetamide;

lxi. 3-[(benzyloxycarbonyl)amino]-7-piperidinyl-quinolin-2-one-N-[1-(2-(5-(3-methylbenzyl)-1,3,4-oxadiazolyl)carbonyl)-2-(S)-methyl]propyl]acetamide;

lxii. 3-(carbomethoxy-quinolin-2-one-N-[1-(2-(5-(3-methybenzyl)-1,3,4-oxadiazolyl)carbonyl)-2-(S)-methylpropyl]acetamide;

lxiii. 3-(amino-quinolin-2-one)-N-[1-(2-(5-(3-methylbenzyl)-1,3,4-oxadiazolyl)carbonyl)-2-(S)-methylpropyl]acetamide;

lxiv. 3-[(4-morpholino)aceto]amino-quinolin-2-one-N-[1-(2-(5-(3-methylbenzyl)-1,3,4-oxadiazolyl)carbonyl)-2-(S)-methylpropyl]acetamide;

lxv. 3,4-dihydro-quinolin-2-one-N-[1-(2-(5-(3-methylbenzyl)-1,3,4-oxadiazolyl)carbonyl)-2-(S)-methylpropyl]acetamide;

lxvi. 1-acetyl-3-(4-fluorobenzylidene)piperazine-2,5-dione-N-[1-(2-(5-(3-methylbenzyl)-1,3,4-oxadiazolyl)carbonyl-2-(S)-methylpropyl]acetamide;

lxvii, 1-acetyl-3-(4-dimethylaminobenzylidene)piperazine-2,5-dione-N-[1-(2-(5-(3-methylbenzyl)-1,3,4-oxadiazolyl)carbonyl)-2-(S)-methylpropyl]acetamide;

lxviii. 1-acetyl-3-(4-carbomethoxybenzylidene)piperazine-2,5-dione-N-[1-(2-(5-(3-methylbenzyl-1,3,4-oxadiazolyl)carbonyl)-2-(S)-methylpropyl]acetamide;

lxix. 1-acetyl-3-[(4-pyridyl)methylene]piperazine-2,5-dione-N-[1-(2-(5-(3-methylbenzyl)-1,3,4-oxadiazolyl)carbonyl)-2-(S)-methylpropyl]acetamide;

lxx. 4-[1-benzyl-3-(R)-benzyl-piperazine-2,5-dione]-N-[1-(2-[5-(3-methylbenzyl)-1,3,4-oxadiazolyl)carbonyl)-2S)-methylpropyl]acetamide;

lxxi. 4-[1-benzyl-3-(S)-benzyl]piperazine-2,5-dione]-N-[1-(2-(5-(3-methylbenzyl)-1,3,4-oxadiazolyl)carbonyl)-2-(S)-methylpropyl]acetamide;

lxxii. 4-[1-benzyl-3-(S)-benzylpiperazine-2,5-dione]-N-[1-(3-(5-(3-trifluoromethylbenzyl)-1,2,4-oxadiazolyl)carbonyl)-2-(S)-methylpropyl]acetamide;

lxxiii. 4-[1-benzyl-3-(S)-benzylpiperazine-2,5-dione]-N-[1-(3-(5-(3-trifluoromethylbenzyl-1,2,4-oxadiazolyl)carbonyl)-2-(S)-methylpropyl]acetamide;

lxxiv. 4-[1-benzyl-3-(S)-benzylpiperazine-2,5-dione]-N-[1-(3-(5-(2-dimethylaminoethyl)-1,2,4-oxadiazolyl)carbonyl)-2-(S)-methylpropyl]acetamide;

lxxv. 4-[1-methyl-3-(R,S)-phenylpiperazine-2,5-dione]-N-[1-(3-(5-(3-trifluoromethylbenzyl)-1,2,4-oxadiazolyl)carbonyl)-2-(S)-methylpropyl]acetamide;

lxxvi. 4-[methyl-3-(R,S)-phenylpiperazine-2,5-dione]-N-[1-(2-(5-(3-methylbenzyl)-1,3,4-oxadiazolyl)carbonyl)-2-(S)-methylpropyl]acetamide;

lxxvii. 4-[1-(4-morpholinoethyl)-3-(R)-benzylpiperazine-2,5-dione]-N-[1 2-(5-(3-methylbenzyl)-1,3,4-oxadiazolyl)carbonyl)-2-(S)-methylpropyl]acetamide;

lxxviii. 5-(RS)-phenyl-2,4-imidazolidinedione-N-[1-(2-(5-(3-methylbenzyl)-1,3,4-oxadiazolyl)carbonyl)-2-(S)-methylpropyl]acetamide;

lxxix. 5-(R)-benzyl-2,4imidazolidinedione-N-[1-(2-(5-(3-methylbenzyl)-1,3,4-oxadiazolyl)carbonyl)-2-(S)-methylpropyl]acetamide;

lxxx. 5-(S)-benzyl-2,4-imidazolidinedione-N-[1-(2-(5-(3-methylbenzyl)-1,3,4-oxadiazolyl)carbonyl)-2-(S)-methylpropyl]acetamide;

lxxxi. 5-(S)-benzyl-2,4-imidazolidinedione-N-[1-(3-(5-(3-trifluoromethylbenzyl)-1,2,4-oxadiazolyl)carbonyl)-2-(S)-methylpropyl]acetamide;

lxxxii. 5-(R)-benzyl-2,4-imidazolidinedione-N-[1-(3-(5-(3-trifluoromethylbenzyl)-1,2,4-oxadiazolyl)carbonyl)-2-(S)-methylpropyl]acetamide;

lxxxiii. 1-benzyl-4-(R)-benzyl-2,5-imidazolidinedione-N-[1-(2-(5-(3-methylbenzyl)-1,3,4-oxadiazolyl)carbonyl)-2(S)-methylpropyl]acetamide;

lxxxiv. 1-benzyl-4-(R)-benzyl-2,5-imidazolidinedione-N-[1-(3-(5-(3-trifluoromethylbenzyl) 1,2,4-oxadiazolyl)carbonyl)-2-(S)-methylpropyl]acetamide, or pharmaceutically acceptable salts thereof, or combinations thereof [Benzyloxycarbonyl-L-valyl-N-[1-(2-(3-methylbenzyl)-1,3,4-oxadiazolyl]carbonyl)-2-(S)-methylpropyl]-L-prolinamide (CE-2072) or a derivative thereof] that upon administration to a patient in need thereof, inhibits serine protease; and at least one second compound selected from the group consisting of HIV reverse transcriptase inhibitors and HIV protease inhibitors, for a time and under conditions effective to inhibit HIV replication.

2. The method according to claim 1 wherein the reverse transcriptase inhibitor is selected from the group consisting of RETROVIR, COMBIVIR, EPIVIR, VIDEX, HIVMD, ZERIT, ZIAGEN, HYDREA, VIRAMUNE, RESCRIPTOR, SUSTIVA, PREVEON, and combinations thereof.

3. The method according to claim 1 wherein the HIV protease inhibitor is selected from the group consisting of FORTOVASE, NORVIR, CRIXIVAN, VIRACEPT, ANGENERASE, VX-478, KNI-272, CGP-61755, u-103017, and combinations thereof.

4. A method of inhibiting human immunodeficiency virus (HIV) replication comprising administering to a patient in need thereof, a combination of at least one compound exhibiting $\alpha_1$-antitrypsin (AAT)-like protease inhibiting activity and one or more compounds selected from a group consisting of HIV reverse transcriptase inhibitors and HIV protease inhibitors, for a time and under conditions effective to inhibit HIV replication, wherein said compound exhibiting AAT-like protease inhibiting activity is i. (benzyloxycarbonyl)-L-valyl-N-[1-(3-(5-(3-trifluoromethylbenzyl)-1,2,4-oxadiazolyl)carbonyl)-2-(S)-methylpropyl]-L-prolinamide;

ii. (benzyloxycarbonyl)-L-valyl-N-[1-(3-(5-(2-phenylethyl)-1,2,4-oxadiazolyl)carbonyl)-2-(S)-methylpropyl]-L-prolinamide;

iii. (benzyloxycarbonyl)-L-valyl-N-[1-(3-(5-(2-methoxybenzyl)-1,2,4-oxadiazolyl)carbonyl)-2-(S)-methylpropyl]-L-prolinamide;

iv. (benzyloxycarbonyl)-L-valyl-N-[1-(3-(5-(trifluoromethyl)-1,2,4-oxadiazolyl)carbonyl)-2-(S)-methylpropyl]-L-prolinamide;

v. (benzyloxycarbonyl)-L-valyl-N-[1-(3-(5-(methyl)-1,2,4-oxadiazolyl)carbonyl)-2-(S)-methylpropyl]-L-prolinamide;

vi. (benzyloxycarbonyl)-L-valyl-N-[1-(3-(5-(difluoromethyl)-1,2,4-oxadiazolyl)carbonyl)-2-(S)-methylpropyl]-L-prolinamide;

vii. (benzyloxycarbonyl)-L-valyl-N-[1-(3-(5-(benzyl)-1,2,4-oxadiazolyl)carbonyl)-2-(S)-methylpropyl]-L-prolinamide;

viii. (benzyloxycarbonyl)-L-valyl-N-[1-(3-(5-(3-methoxybenzyl)-1,2,4-oxadiazolyl)carbonyl)-2-(S)-methylpropyl]-L-prolinamide;

ix. (benzyloxycarbonyl)-L-valyl-N-[1-(3-(5-(2,6-difluorobenzyl)-1,2,4-oxadiazolyl)carbonyl)-2-(S)-methylpropyl]-L-prolinamide;

x. (benzyloxycarbonyl)-L-valyl-N-[1-(3-(5-(trans-styryl)-1,2,4-oxadiazolyl)carbonyl)-2-(S)-methylpropyl]-L-prolinamide;

xi. (benzyloxycarbonyl)-L-valyl-N-[1-(3-(5-(trans-4-trifluoromethylstyryl)-1,2,4-oxadiazolyl)carbonyl)-2-(S)-methylpropyl]-L-prolinamide;

xii. (benzyloxycarbonyl)-L-valyl-N-[1-(3-(5-(trans-4-methoxystyryl)-1,2,4-oxadiazolyl)carbonyl)-2-(S)-methylpropyl]-L-prolinamide;

xiii. (benzyloxycarbonyl)-L-valyl-N-[1-(3-(5-(3-thienylmethyl)-1,2,4-oxadiazolyl)carbonyl)-2-(S)-methylpropyl-L-prolinamide;

xiv. (benzyloxycarbonyl)-L-valyl-N-[1-(3S-(phenyl)-1,2,4-oxadiazolyl carbonyl)-2-(S)-methylpropyl]-L-prolinamide;

xv. (benzyloxycarbonyl)-L-valyl-N-[1-(3-(5-(3-phenylpropyl)-1,2,4-oxadiazolyl)carbonyl)-2-(S)-methylpropyl]-L-prolinamide;

xvi. (benzyloxycarbonyl)-L-valyl-N-[1-(2-(3-(methylbenzyl)-1,3,4-oxadiazolyl)carbonyl)-2-(S)-methylpropyl]-L-prolinamide;

xvii. (benzyloxycarbonyl)-L-valyl-N-[1-(2-(5-(methyl)-1,3,4-oxadiazolyl]carbonyl)-2-(S)-methylpropyl]-L-prolinamide;

xviii. (benzyloxycarbonyl)-L-valyl-N-[1-(2-(5-(3-trifluoromethylbenzyl)-1,3,4-oxadiazolyl)carbonyl)-2-(S)-methylpropyl-L-prolinamide;

xix. (benzyloxycarbonyl)-L-valyl-N-[1-(2-(5-(4-dimethylaminobenzyl)-1,3,4-oxadiazoly]carbonyl-2-(S)-methylpropyl]-L-prolinamide;

xx. (benzyloxycarbonyl)-L-valyl-N-[1-(2-(5-(1-napthylenyl)-1,3,4-oxadiazolyl)carbonyl)-2-(S)-methylpropyl]-L-prolinamide;

xxi. (benzyloxycarbonyl)-L-valyl-[1-(3-(5-(3,4-methylenedioxybenzyl)-1,2,4-oxadiazolyl)carbonyl)-2-(S)-methylpropyl]-L-prolinamide;

xxii. (benzyloxycarbonyl)-L-valyl-N-[1-(3-(3-(5-(3,5 dimethylbenzyl)-1,2,4-oxadiazolyl)carbonyl)-2-(S)-methylpropyl]-L-prolinamide;

xxiii. (benzyloxycarbonyl)-L-valyl-N-[1-(3-(5-(3,5-dimethoxybenzyl)-1,2,4-oxadiazolyl)carbonyl)-2-(S)-methylpropyl]-L-prolinamide;

xxiv. (benzyloxycarbonyl)-L-valyl-N-[1-(3-(5-(3,5-ditrifluoromethylbenzyl)-1,2,4-oxadiazolyl)carbonyl)-2-(S)-methylpropyl]-L-prolinamide;

xxv. (benzyloxycarbonyl)-L-valyl-N-[1-(3-(5-(3-methylbenzyl)-1,2,4-oxadiazolyl)carbonyl)-2-(S)-methylpropyl]-L-prolinamide;

xxvi. (benzyloxycarbonyl)-L-valyl-N-r 1-(3-(5-(biphenylmethine)-1.2,4-oxadiazolyl)carbonyl)-2-(S)-methylpropyl]-Lprolinamide;

xxvii. (benzyloxycarbonyl)-L-valyl-N-[1-(3-(5-(4-phenylbenzyl)-1,2,4-oxadiazolyl)carbonyl)-2-(S)-methylpropyl]-L-prolinamide;

xxiii. (benzyloxycarbonyl)-L-valyl-N-[1-(3-(5-(3-phenylbenzyl)-1,2,4-oxadiazolyl)carbonyl)-2-(S)-methylpropyl]-L-prolinamide;

xxix. (benzyloxycarbonyl)-L-valyl-N-[1-(3-(5-(3-phenoxybenzyl)-1,2,4-oxadiazolyl)carbonyl)-2-(S)-methylpropyl]-L-prolinamide;

xxx. (benzyloxycarbonyl)-L-valyl-N-[1-(3-(5-(cyclohexylmethylene)-1,2,4-oxadiazolyl)carbonyl-2-(S)-methylpropyl]-L-prolinamide;

xxxi. (benzyloxycarbonyl)-L-valyl-N-[1-(3-(5-(3-trifluoromethyldimethylmethylene)-1,2,4-oxadiazolyl)carbonyl)2-(S)-methylpropyl-L-prolinamide;

xxxii. (benzyloxycarbonyl)-L-valyl-N-[1-(3-(5-(1-napthylmethylene)-1,2,4-oxadiazolyl)carbonyl)-2-(S)-methylpropyl]-L-prolinamide;

xxxiii. (benzyloxycarbonyl)-L-valyl-N-[1-(3-(5-(3-pyridylmethyl)-1,2,4-oxadiazolyl)carbonyl)-2-(S)-methylpropyl]-L-prolinamide;

xxxiv. (benzyloxycarbonyl)-L-valyl-N-[1-(3-(5-(3,5-diphenylbenzyl)-1,2,4-oxadiazolyl)carbonyl)-2-(S)-methylpropyl]-L-prolinamide;

xxxv. (benzyloxycarbonyl)-L-valyl-N-[1-(3-(5-(4-dimethylaminobenzyl)-1,2,4-oxadiazolyl)carbonyl)-2-(S)-methylpropyl-L-prolinamide;

xxxvi. 2-(5-[(benzyloxycarbonyl)amino]-6-oxo-2-(4-fluorophenyl)-1,6dihydro-1-pyrimidinyl]-N-[1-(3-(5-(3-trifluoromethylbenzyl)-1,2,4-oxadiazolyl)carbonyl)-(S)-2-methylpropyl]acetamide;

xxxvvii. 2-(5-amino-6-oxo-2-(4-fluorophenyl)-1,6-dihydro-1-pyrimidinyl]-N-[1-3-(5-(3-trifluoromethylbenzyl)-1,2,4-oxadiazolyl)carbonyl)-2-(S)-methylpropyl]acetamide;

xxxviii. 2-[5-[(benzyloxycarbonyl)amino]-6-oxo-2-(4-fluorophenyl)-1.6-dihydro-1-pyrimidinyl]-N-[1-(2-(5-(3-methylbenzyl)-1,3,4-oxadiazolyl)carbonyl)-(S)-2-methylpropyl]acetamide;

xxxix. 2-[5-amino-6-oxo-2-(4-fluorophenyl)-1,6-dihydro-1-pyrimidinyl]-N-[1-(2-(5-(3-methylbenzyl)-1,3,4-oxadiazolyl)carbonyl)-2-methylpropyl]acetamide;

xl. (pyrrole-2-carbonyl)-N-(benzyl)glycyl-N-[1-(2-(5-(3-methylbenzyl)-1,3,4-oxadiazolyl)carbonyl)-2-(S)-methylpropyl]amide;

xli. (pyrrole-2-carbonyl)-N-(benzyl)glycyl-N-[1-(3-(5-(3-trifluoromethylbenzyl)(1,2,4-oxadiazolyl)-(S)-methylpropyl]amide;

xlii. (2S, 5S)-5-amino-1,2,4,5,6,7-hexahydroazepino-[3,2,1]-indole-4-one-carbonyl-N-[1-(2-(5-(3-methylbenzyl)-1,3,4-oxadiazolyl)carbonyl)-(R,S)-2-methylpropyl]amide;

xliii. BTD-[1-(2-(5-(3-methylbenzyl)-1,3,4-oxadiazolyl)carbonyl)-2-(S)methylpropyl]amide;

xliv. (R,S)-3-amino-2-oxo-5-phenyl-1,4-benzodiazepine-N-[1-(2-(5-(3-methylbenzyl)-1,3,4-oxadiazolyl)carbonyl)-2-(S)-methylpropyl]acetamide;

xlv. (benzyloxycarbonyl)-L-valyl-2-L-(2.3-dihydro-1H-indole)-N-[1-(2-(5-(3-methylbenzyl)-1,3,4-oxadiazolyl)carbonyl)-2-(S)-methylpropyl]amide;

xlvi. (benzyloxycarbonyl)-L-valyl-2-L-(2,3-dihydro-1H-indole)-N-[1-(3-(5-(3-trifluoromethylbenzyl)-1,2,4-oxadiazolyl)carbonyl)-2-(S)methylpropyl]amide;

xlvii. acetyl-2-L-(2,3-dihydro-1H-indole)-N-r 1-(2-(5-(3-methylbenzyl)-1,3,4-oxadiazolyl)carbonyl)-2-(S)-methylpropyl]amide;

xlviii. 3-(S)-(benzyloxycarbonyl)amino)-e-lactam-N-[1-(2-(5-(3-methylbenzyl)-1,3,4-oxadiazolyl)carbonyl)-2-(S)-methylpropyl acetamide;

xlix. 3-(S)-(amino)-e-lactam-N-[1-(2-(5-(3-methylbenzyl)-1,3,4-oxadiazolyl)carbonyl)-2-(S)-methylpropyl]acetamide trifluoroacetic acid salt;

1. 3-(S)-[(4-morpholinocarbonyl-butanol)amino]-e-lactam-N-[1-(2-(5-(3-methylbenzyl)-1,3,4-oxadiazolyl)carbonyl)-2-(R,S)-methylpropyl]acetamide;

li. 6-[4-fluorophenyl]-e-lactam-N-[1-(2-(5-(3-methylbenzyl)-1,3,4-oxadiazolyl)carbonyl)-2-(S)-methylpropyl]acetamide;

lii. 2-(2-(R,S)-phenyl-4-oxothiazolidin-3-yl]-N-[1-(2-(5-(3-methylbenzyl)-1,3,4-oxadiazolyl)carbonyl)-2-(S)-methylpropyl]acetamide;

liii. 2-(2-(R,S)-phenyl-4-oxothiazolidin-3-yl]-N-[1-(2-(5-(3-methylbenzyl)-1,3,4-oxadiazolyl(hydroxymethyl)2-(S)-methyl]propyl]acetamide;

liv. 2-(2-(R,S)-benzyl-4-oxothiazolidin-3-yl]-N-[1-(2-(5-(3-methylbenzyl)-1,3,4-oxadiazolyl]carbonyl)-2-(S)-methylpropyl]acetamide;

lv. 2-(2-(R,S)-benzyl-4-oxothiazolidin-3-yl oxide]-N-[1-(3-(5-(3-trifluoromethylbenzyl-1,2,4-oxadiazolyl)carbonyl)-2-(R,S,)-methylpropyl]acetamide;

lvi. (1-benzoyl-3,8-quinazolinedione)-N-[1-(2-(5-(3-methylbenzyl)-1,3,4-oxadiazolyl)carbonyl)-2-(S)-methylpropyl]acetamide;

lvii. (1-benzoyl-3,6-piperazinedione)-N-[1-(2-(5-(3-methylbenzyl)-1,3,4-oxadiazolyl)carbonyl)-2-(S)-methylpropyl]acetamide;

lvii. (1-phenyl-3,6-piperazinedione)-N-[1-(2-(5-(3-methylbenzyl)-1,3,4-oxadiazolyl)carbonyl)-2-(S)-methylpropyl]acetamide;

lix. (1-phenyl-3-piperazinedione)-N-[1-(3-(5-(3-trifluoromethylbenzyl)-1,2,4-oxadiazolyl)carbonyl)]-2-(S)-methylpropyl]acetamide;

lx. 3-[(benzyloxycarbonyl)amino]-quinolin-2-one-N-[1-(2-(5-(3-methylbenzyl) 1,3,4-oxadiazolyl)carbonyl)-2-(S)-methylpropyl]acetamide;

lixi. 3-[(benzyloxycarbonyl)amino]-7-piperidinyl-quinolin-2-one-N-[1-(2-(5-(3-methylbenzyl)-1,3,4-oxadiazolyl)carbonyl)-2-(S)-methlpropyl]acetamide;

lxii. 3-(carbomethoxy-quinolin-2-one-N-[1-(2-(5-(3-methybenzyl)-1,3,4-oxadiazolyl)carbonyl)-2-(S)-methylpropyl]acetamide;

lxiii. 3-(amino-quinolin-2-one)-N-[1-(2-(5-(3-methylbenzyl)-1,3,4-oxadiazolyl)carbonyl)-2-(S)-methylpropyl]acetamide;

lxiv. 3-[(4-morpholino)aceto]amino-quinolin-2-one-N-[1-(2-(5-(3-methylbenzyl 1,3,4-oxadiazol)carbonyl)-2-(S)-methylpropyl]acetamide;

lxv. 3,4-dihydro-quinolin-2-one-N-[1-(2-(5-(3-methylbenzyl)-[1,3,4-oxadiazolyl)carbonyl)-2-(S)-methylpropyl]acetamide;

lxvi. 1-acetyl-3-(4-fluorobenzylidene)piperazine-2,5-dione-N-[1-(2-(5-(3-methylbenzyl)-1,3,4-oxadiazolyl)carbonyl)-2-(S)-methylpropyl]acetamide;

lxvii. 1-acetyl-3-(4-dimethylaminobenzylidene)piperazine-2.5-dione-N-[1-(2-(5-(3-methylbenzyl)-1,3,4-oxadiazolyl)carbonyl)-2-(S)-methylpropyl]acetamide;

lxviii. 1-acetyl-3-(4-carbomethoxybenzylidene)piperazine-2,5-dione-N-rl-(2-(5-(3-methylbenzyl)-1,3,4-oxadiazolyl)carbonyl)-2-(S)-methylpropyl]acetamide;

lxix. 1-acetyl-3-[(4-pyridyl)methylene]piperazine-2.5-dione-N-[1-(2-(5-(3-methylbenzyl)-1,3,4-oxadiazolyl)carbonyl)-2-(S)-methylpropyl]acetamide;

lxx. 4-[1-benzyl-3-(R)-benzyl-piperazine-2,5-dione]-N-[1-(2-[5-(3-methylbenzyl)-1,3,4-oxadiazolyl)carbonyl)-2-(S)-methylpropyl]acetamide;

lxxi. 4-[1-benzyl-3-(S)-benzylpiperazine-2,5-dione]-N-[1-(2-(5-(3-methylbenzyl)-1,3,4-oxadiazolyl)carbonyl)-2-(S)-methylpropyl]acetamide;

lxxii. 4-[1-benzyl-3(R)-benzylpiperazine-2,5-dione]-N-[1-(3-(5-(3-trifluoromethylbenzyl)-1,2,4-oxadiazolyl)carbonyl)-2-(S)-methylpropyl]acetamide;

lxxiii. 4-[1-benzyl-3-(S)-benzylpiperazine-2,5-dione]-N-[1-(3-(5-3-trifluoromethylbenzyl)-1,2,4-oxadiazolyl)carbonyl)-2-(S)-methylpropyl]acetamide;

lxxiv. 4-[1-benzyl-3-(S)-benzylpiperazine-2,5-dione]-N-[1-(3-(5-(2-dimethylaminoethyl)-1,2,4-oxadiazolyl)carbonyl)-2-(S)-methylpropyl]acetamide;

lxxv. 4-[1-methyl-3-(R,S)-phenylpiperazine-2,5-dione]-N-[1-(3-(5-(3-trifluoromethylbenzyl)-1,2,4-oxadiazolyl)carbonyl)-2-(S)-methylpropyl]acetamide;

lxxvi. 4-[methyl-3-(R,S)-phenylpiperazine-2.5-dione]-N-[1-(2-(5-(3-methylbenzyl)-1,3,4-oxadiazolyl)carbonyl)-2-(S)-methylpropyl]acetamide;

lxxvii. 4-[4-morpholinoethyl)-3-(R)-benzylpiperazine-2,5-dione]-N-[1-(2-(5-(3-methylbenzyl)-1,3,4-oxadiazolyl)carbonyl)-2-(S)-methylpropyl]acetamide;

lxxiviii. 5-(R,S)-phenyl-2,4-imidazolidinedione-N-[1 1-(2-(5-(3-methylbenzyl)-1,3,4-oxadiazolyl)carbonyl)-2-(S)-methylpropyl]acetamide;

lxxix. 5-(R)-benzyl-2,4-imidazolidinedione-N-[1-(2-(5-(3-methylbenzyl)-1,3,4-oxadiazolyl)carbonyl)-2-(S)-methylpropyl]acetamide;

lxxx. 5-(S)-benzyl-2,4-imidazolidinedione-N-[1-(2-(5-(3-methylbenzyl)-1,3.4-oxadiazolyl)carbonyl)-2-(S)-methylpropyl]acetamide;

lxxxi. 5-(S)-benzyl-2,4-imidazolidinedione-N-[1-(3-(5-(3-trifluoromethylbenzyl)-1,2,4-oxadiazolyl)carbonyl)-2-(S)-methylpropyl]acetamide;

lxxxii. 5-(R)-benzyl-2,4-imidazolidinedione-N-(1-(3-(5-(3-trifluoromethylbenzyl)-1,2,4-oxadiazolyl)carbonyl)-2-(S)-methylpropyl]acetamide;

lxxxiii. 1-benzyl-4-benzyl-2.5-imidazolidinedione-N-[1-(2-(5-(3-methylbenzyl)-1,3,4-oxadiazolyl)carbonyl)-2-(S)-methylpropyl]acetamide;

lxxxiv. 1-benzyl-4-(R)-benzyl-2,5-imidazolidinedione-N-[1-(3-(5-(3-trifluoromethylbenzyl) 1,2,4-oxadiazolyl)carbonyl)-2-(S)-methylpropyl]acetamide, or pharmaceutically acceptable salts thereof, or combinations thereof

[a non-natural molecule comprising Benzyloxycarbonyl-L-valyl-N-[1-(2-(3-methylbenzyl)-1,3,4-oxadiazolyl]carbonyl)-2-(S)-methylpropyl]-L-prolinamide (CE-2072) or a derivative thereon that, upon administration to a patient in need thereof, inhibits serine protease.

* * * * *